United States Patent
Kahn et al.

(10) Patent No.: US 11,058,350 B1
(45) Date of Patent: Jul. 13, 2021

(54) TRACKING AND PROMPTING MOVEMENT AND ACTIVITY

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 14/918,540

(22) Filed: Oct. 20, 2015

Related U.S. Application Data

(63) Continuation of application No. 14/509,043, filed on Oct. 7, 2014, now abandoned, which is a continuation
(Continued)

(51) Int. Cl.
*A61B 5/00* (2006.01)
*H04B 1/3827* (2015.01)
(Continued)

(52) U.S. Cl.
CPC ............ *A61B 5/486* (2013.01); *A61B 5/1118* (2013.01); *A61B 5/222* (2013.01); *A61B 5/4812* (2013.01);
(Continued)

(58) Field of Classification Search
CPC .......... A61B 5/4812; A61B 2562/0219; A61B 5/1118; A61B 5/11; A61B 5/4809;
(Continued)

(56) References Cited

U.S. PATENT DOCUMENTS

| | | |
|---|---|---|
| 2,082,843 A | 6/1937 | Mathez |
| 3,541,781 A | 11/1970 | Bloom |
| (Continued) | | |

FOREIGN PATENT DOCUMENTS

| | | |
|---|---|---|
| AU | 2003203967 A1 | 11/2004 |
| CH | 377738 A | 1/1964 |
| (Continued) | | |

OTHER PUBLICATIONS

"Fitbit Product Manual", <http://www.fitbit.com/manual>, Last updated Mar. 29, 2010, 20 pages.
(Continued)

*Primary Examiner* — Jack Yip
(74) *Attorney, Agent, or Firm* — Nicholson De Vos Webster & Elliott LLP; Judith Szepesi

(57) ABSTRACT

A method of monitoring a user's activity level, and improving the user's health with a wearable device designed to be worn all day. The method comprises in one embodiment determining that the user is wearing the wearable device, and monitoring movements of the user using a motion sensing system in the wearable device. The method further determines when the user has not moved in a period of time, and alerts the user to move, when the user has not moved from an ergonomic activity in a preset period of time. The method further counts steps taken by a user, and identifies and tracks aerobic exercise activity.

22 Claims, 22 Drawing Sheets

Related U.S. Application Data of application No. 12/819,195, filed on Jun. 19, 2010, now Pat. No. 10,335,060.

(51) Int. Cl.

| | |
|---|---|
| *H04W 4/02* | (2018.01) |
| *H04L 29/08* | (2006.01) |
| *G09B 5/02* | (2006.01) |
| *G09B 19/00* | (2006.01) |
| *A61B 5/22* | (2006.01) |
| *A61B 5/11* | (2006.01) |

(52) U.S. Cl.
CPC .......... *A61B 5/6801* (2013.01); *A61B 5/7246* (2013.01); *G09B 5/02* (2013.01); *G09B 19/00* (2013.01); *H04B 1/385* (2013.01); *H04L 67/02* (2013.01); *H04W 4/027* (2013.01)

(58) Field of Classification Search
CPC ....... A61B 5/486; A61B 5/222; A61B 5/6801; A61B 5/7246; A61M 2021/0083; G09B 5/02; G09B 19/00; H04B 1/385; H04L 67/02; H04W 4/027
See application file for complete search history.

(56) References Cited

U.S. PATENT DOCUMENTS

| | | | |
|---|---|---|---|
| 3,798,889 A | 3/1974 | Chadwick | |
| 4,228,806 A | 10/1980 | Lidow | |
| 4,297,685 A | 10/1981 | Brainard, II | |
| 4,322,609 A | 3/1982 | Kato | |
| 4,573,804 A | 3/1986 | Kavoussi et al. | |
| 4,788,533 A | 11/1988 | Mequignon | |
| 4,848,360 A | 7/1989 | Palsgard et al. | |
| 4,858,609 A | 8/1989 | Cole | |
| 4,982,738 A | 1/1991 | Griebel | |
| 5,008,865 A | 4/1991 | Shaffer et al. | |
| 5,047,930 A | 9/1991 | Martens et al. | |
| 5,275,159 A | 1/1994 | Griebel | |
| 5,335,657 A | 8/1994 | Terry, Jr. et al. | |
| 5,458,105 A | 10/1995 | Taylor et al. | |
| 5,545,192 A | 8/1996 | Czeisler et al. | |
| 5,562,106 A | 10/1996 | Heeke et al. | |
| 5,671,733 A | 9/1997 | Raviv et al. | |
| 5,844,996 A | 12/1998 | Enzmann et al. | |
| 5,868,647 A * | 2/1999 | Belsole .............. A63B 23/16 482/8 |
| 5,928,133 A | 7/1999 | Halyak | |
| 5,961,447 A | 10/1999 | Raviv et al. | |
| 6,045,514 A | 4/2000 | Raviv et al. | |
| 6,239,706 B1 | 5/2001 | Yoshiike et al. | |
| 6,350,275 B1 | 2/2002 | Vreman et al. | |
| 6,361,508 B1 | 3/2002 | Johnson et al. | |
| 6,468,234 B1 | 10/2002 | Van der Loos et al. | |
| 6,547,728 B1 | 4/2003 | Cornuejols | |
| 6,556,222 B1 | 4/2003 | Narayanaswami | |
| 6,834,436 B2 | 12/2004 | Townsend et al. | |
| 6,888,779 B2 | 5/2005 | Mollicone et al. | |
| 6,928,031 B1 | 8/2005 | Kanevsky et al. | |
| 6,963,271 B1 | 11/2005 | Fyffe | |
| 7,006,650 B1 | 2/2006 | Wild | |
| 7,041,049 B1 | 5/2006 | Raniere | |
| 7,106,662 B1 | 9/2006 | Acker | |
| 7,153,278 B2 | 12/2006 | Ono et al. | |
| 7,280,439 B1 | 10/2007 | Shaddox | |
| 7,366,572 B2 | 4/2008 | Heruth et al. | |
| 7,513,003 B2 | 4/2009 | Mossbeck | |
| 7,559,903 B2 | 7/2009 | Moussavi et al. | |
| 7,572,225 B2 | 8/2009 | Stahmann et al. | |
| 7,841,987 B2 | 11/2010 | Sotos et al. | |
| 7,862,226 B2 | 1/2011 | Bracher et al. | |
| 7,914,468 B2 | 3/2011 | Shalon et al. | |
| 7,974,849 B1 * | 7/2011 | Begole .............. G06Q 10/10 705/1.1 |
| 8,179,270 B2 | 5/2012 | Rai et al. | |
| 8,193,941 B2 | 6/2012 | Wolfe et al. | |
| 8,398,546 B2 | 3/2013 | Pacione et al. | |
| 8,407,835 B1 | 4/2013 | Connor | |
| 8,475,339 B2 | 7/2013 | Hwang et al. | |
| 8,482,418 B1 | 7/2013 | Harman | |
| 8,577,448 B2 | 11/2013 | Bauer et al. | |
| 8,680,974 B2 | 3/2014 | Meiertoberens et al. | |
| 8,738,925 B1 | 5/2014 | Park et al. | |
| 8,892,036 B1 | 11/2014 | Causey et al. | |
| 8,942,719 B1 | 1/2015 | Hyde et al. | |
| 9,060,735 B2 | 6/2015 | Yang et al. | |
| 9,161,719 B2 | 10/2015 | Tsutsumi et al. | |
| 9,448,536 B1 | 9/2016 | Kahn et al. | |
| 9,474,876 B1 | 10/2016 | Kahn et al. | |
| 9,594,354 B1 | 3/2017 | Kahn et al. | |
| 9,675,268 B2 | 6/2017 | Bauer et al. | |
| 9,844,336 B2 | 12/2017 | Zigel et al. | |
| 10,004,452 B2 | 6/2018 | Kazem-Moussavi et al. | |
| 10,207,075 B1 | 2/2019 | Kahn et al. | |
| 2001/0049482 A1 * | 12/2001 | Pozos ................. A61B 5/1107 600/587 |
| 2002/0080035 A1 | 6/2002 | Youdenko | |
| 2002/0100477 A1 | 8/2002 | Sullivan et al. | |
| 2002/0124848 A1 | 9/2002 | Sullivan et al. | |
| 2003/0095476 A1 | 5/2003 | Mollicone et al. | |
| 2003/0204412 A1 | 10/2003 | Brier | |
| 2003/0227439 A1 | 12/2003 | Lee et al. | |
| 2003/0231495 A1 | 12/2003 | Searfoss | |
| 2004/0034289 A1 | 2/2004 | Teller et al. | |
| 2004/0049132 A1 | 3/2004 | Barron et al. | |
| 2004/0133081 A1 * | 7/2004 | Teller ...................... A61B 5/01 600/300 |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0043645 A1 | 2/2005 | Ono et al. | |
| 2005/0075116 A1 | 4/2005 | Laird et al. | |
| 2005/0143617 A1 | 6/2005 | Auphan | |
| 2005/0154330 A1 | 7/2005 | Loree | |
| 2005/0190065 A1 | 9/2005 | Ronnholm | |
| 2005/0236003 A1 | 10/2005 | Meader | |
| 2005/0237479 A1 | 10/2005 | Rose | |
| 2005/0245793 A1 | 11/2005 | Hilton et al. | |
| 2005/0283039 A1 | 12/2005 | Cornel | |
| 2005/0288904 A1 | 12/2005 | Warrior et al. | |
| 2006/0017560 A1 | 1/2006 | Albert | |
| 2006/0025299 A1 | 2/2006 | Miller et al. | |
| 2006/0064037 A1 * | 3/2006 | Shalon ................ A61B 5/0006 600/586 |
| 2006/0097884 A1 | 5/2006 | Jang | |
| 2006/0136018 A1 | 6/2006 | Lack et al. | |
| 2006/0150734 A1 | 7/2006 | Mimnagh-Kelleher et al. | |
| 2006/0252999 A1 | 11/2006 | DeVaul et al. | |
| 2006/0266356 A1 | 11/2006 | Solos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0100666 A1 * | 5/2007 | Stivoric ............ A61B 10/0012 705/3 |
| 2007/0129644 A1 | 6/2007 | Richards et al. | |
| 2007/0139362 A1 * | 6/2007 | Colton ................. G16H 40/67 345/156 |
| 2007/0191692 A1 | 8/2007 | Hsu et al. | |
| 2007/0239225 A1 | 10/2007 | Saringer | |
| 2007/0250286 A1 * | 10/2007 | Duncan ................ A61B 5/1121 702/139 |
| 2007/0251997 A1 | 11/2007 | Brown et al. | |
| 2007/0287930 A1 | 12/2007 | Sutton | |
| 2008/0062818 A1 | 3/2008 | Plancon et al. | |
| 2008/0109965 A1 | 5/2008 | Mossbeck | |
| 2008/0125820 A1 | 5/2008 | Stahmann et al. | |
| 2008/0191885 A1 | 8/2008 | Iv et al. | |
| 2008/0234785 A1 | 9/2008 | Nakayama et al. | |
| 2008/0243014 A1 | 10/2008 | Moussavi et al. | |
| 2008/0275348 A1 * | 11/2008 | Catt ..................... A61B 5/1112 600/483 |

(56) References Cited

U.S. PATENT DOCUMENTS

| | | |
|---|---|---|
| 2008/0289637 A1 | 11/2008 | Wyss |
| 2008/0319277 A1 | 12/2008 | Bradley |
| 2009/0030767 A1* | 1/2009 | Morris .............. G06Q 10/1093 |
| | | 705/7.18 |
| 2009/0048540 A1 | 2/2009 | Otto et al. |
| 2009/0069644 A1 | 3/2009 | Hsu et al. |
| 2009/0082699 A1 | 3/2009 | Bang et al. |
| 2009/0094750 A1 | 4/2009 | Oguma et al. |
| 2009/0105785 A1 | 4/2009 | Wei et al. |
| 2009/0121826 A1 | 5/2009 | Song et al. |
| 2009/0128487 A1 | 5/2009 | Langereis et al. |
| 2009/0143636 A1 | 6/2009 | Mullen et al. |
| 2009/0150217 A1* | 6/2009 | Luff .................. G06Q 30/0203 |
| | | 705/7.32 |
| 2009/0177327 A1 | 7/2009 | Turner et al. |
| 2009/0203970 A1 | 8/2009 | Fukushima et al. |
| 2009/0207028 A1 | 8/2009 | Kubey et al. |
| 2009/0227888 A1 | 9/2009 | Salmi et al. |
| 2009/0264789 A1* | 10/2009 | Molnar .............. A61N 1/36135 |
| | | 600/544 |
| 2009/0320123 A1 | 12/2009 | Yu et al. |
| 2010/0010330 A1 | 1/2010 | Rankers et al. |
| 2010/0061596 A1 | 3/2010 | Mostafavi et al. |
| 2010/0075807 A1 | 3/2010 | Hwang et al. |
| 2010/0079291 A1* | 4/2010 | Kroll .................. G06F 19/3481 |
| | | 340/573.1 |
| 2010/0079294 A1 | 4/2010 | Rai et al. |
| 2010/0083968 A1* | 4/2010 | Wondka .............. A61M 16/125 |
| | | 128/204.23 |
| 2010/0094148 A1 | 4/2010 | Bauer et al. |
| 2010/0100004 A1 | 4/2010 | Someren |
| 2010/0102971 A1 | 4/2010 | Virtanen et al. |
| 2010/0152543 A1 | 6/2010 | Heneghan et al. |
| 2010/0152546 A1 | 6/2010 | Behan et al. |
| 2010/0217146 A1 | 8/2010 | Osvath |
| 2010/0256512 A1 | 10/2010 | Sullivan |
| 2010/0283618 A1 | 11/2010 | Wolfe et al. |
| 2010/0331145 A1 | 12/2010 | Lakovic et al. |
| 2011/0015467 A1 | 1/2011 | Dothie et al. |
| 2011/0015495 A1* | 1/2011 | Dothie .................. G16H 10/60 |
| | | 600/300 |
| 2011/0018720 A1 | 1/2011 | Rai et al. |
| 2011/0054279 A1 | 3/2011 | Reisfeld et al. |
| 2011/0058456 A1 | 3/2011 | De et al. |
| 2011/0090226 A1 | 4/2011 | Sotos et al. |
| 2011/0105915 A1 | 5/2011 | Bauer et al. |
| 2011/0137836 A1 | 6/2011 | Kuriyama et al. |
| 2011/0160619 A1 | 6/2011 | Gabara |
| 2011/0190594 A1 | 8/2011 | Heit et al. |
| 2011/0199218 A1 | 8/2011 | Caldwell et al. |
| 2011/0230790 A1 | 9/2011 | Kozlov |
| 2011/0245633 A1* | 10/2011 | Goldberg .............. A61B 5/486 |
| | | 600/301 |
| 2011/0295083 A1 | 12/2011 | Doelling et al. |
| 2012/0004749 A1 | 1/2012 | Abeyratne et al. |
| 2012/0083715 A1 | 4/2012 | Yuen et al. |
| 2012/0232414 A1 | 9/2012 | Mollicone et al. |
| 2012/0243379 A1 | 9/2012 | Balli |
| 2012/0253220 A1 | 10/2012 | Rai et al. |
| 2012/0296156 A1 | 11/2012 | Auphan |
| 2013/0012836 A1 | 1/2013 | Veiga et al. |
| 2013/0018284 A1 | 1/2013 | Kahn et al. |
| 2013/0023214 A1 | 1/2013 | Wang et al. |
| 2013/0053653 A1 | 2/2013 | Cuddihy et al. |
| 2013/0053656 A1 | 2/2013 | Mollicone et al. |
| 2013/0060306 A1 | 3/2013 | Colbauch |
| 2013/0144190 A1 | 6/2013 | Bruce et al. |
| 2013/0184601 A1 | 7/2013 | Zigel et al. |
| 2013/0204314 A1 | 8/2013 | Miller et al. |
| 2013/0208576 A1 | 8/2013 | Loree et al. |
| 2013/0286793 A1 | 10/2013 | Umamoto |
| 2013/0289419 A1 | 10/2013 | Berezhnyy et al. |
| 2013/0310658 A1 | 11/2013 | Ricks et al. |
| 2014/0005502 A1 | 1/2014 | Klap et al. |
| 2014/0051938 A1 | 2/2014 | Goldstein et al. |
| 2014/0085077 A1* | 3/2014 | Luna .................. G08B 6/00 |
| | | 340/539.11 |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0219064 A1 | 8/2014 | Filipi et al. |
| 2014/0232558 A1 | 8/2014 | Park et al. |
| 2014/0256227 A1 | 9/2014 | Aoki et al. |
| 2014/0259417 A1 | 9/2014 | Nunn et al. |
| 2014/0259434 A1 | 9/2014 | Nunn et al. |
| 2014/0276227 A1 | 9/2014 | Pérez |
| 2014/0288878 A1 | 9/2014 | Donaldson |
| 2014/0306833 A1 | 10/2014 | Ricci |
| 2014/0371635 A1 | 12/2014 | Shinar et al. |
| 2015/0068069 A1 | 3/2015 | Tran et al. |
| 2015/0073283 A1 | 3/2015 | Vugt et al. |
| 2015/0085622 A1 | 3/2015 | Carreel et al. |
| 2015/0098309 A1 | 4/2015 | Adams et al. |
| 2015/0141852 A1 | 5/2015 | Dusanter et al. |
| 2015/0148871 A1 | 5/2015 | Maxik et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0233598 A1 | 8/2015 | Shikii et al. |
| 2015/0265903 A1 | 9/2015 | Kolen et al. |
| 2015/0289802 A1 | 10/2015 | Thomas et al. |
| 2017/0003666 A1 | 1/2017 | Nunn et al. |

FOREIGN PATENT DOCUMENTS

| | | |
|---|---|---|
| CH | 668349 A | 12/1988 |
| CH | 697528 B1 | 11/2008 |
| DE | 19642316 A1 | 4/1998 |
| EP | 1139187 B1 | 10/2010 |
| JP | 8160172 | 6/1996 |
| JP | 2007132581 A | 5/2007 |
| KR | 1020100022217 A | 3/2010 |
| KR | 1020009085403 | 6/2011 |
| WO | 9302731 A1 | 2/1993 |
| WO | 2008038288 A3 | 5/2009 |
| WO | 2009099292 A2 | 8/2009 |
| WO | 2011141840 A1 | 11/2011 |

OTHER PUBLICATIONS

"How BodyMedia FIT Works", <http://www.bodymedia.com/Shop/Learn-More/How-it-works, accessed Jun. 17, 2011, 2 pages.

David F. Dinges, <en.wikipedia.org/wiki/David_Dinges>, Last Modified Sep. 12, 2012, 2 pages.

Jaines, Kira, "Music to Help You Fall Asleep," <http://www.livestrong.com/article/119802-music-fall-sleep/>, May 10, 2010, 2 pages.

Jetlog Reviewers Guide, <http://www.jetlog.com/fileadmin/Presse_us/24x7ReviewersGuide.pdf>, 2009, 5 pages.

Leeds, Joshua, "Sound-Remedies.com: Sonic Solutions for Health, Learning & Productivity," <http://www.sound-remedies.com/ammusforslee.html> Accessed May 23, 2013, 2 pages.

Liden, Craig B, et al, "Characterization and Implications of the Sensors Incorporated into the SenseWear(TM) Armband for Energy Expenditure and Activity Detection", <http://www.bodymedia.com/Professionals/Whitepapers/Characterization-and-Implications-of-the-Sensors-Incorporated-into-the-SenseWear>, accessed Jun. 17, 2011, 7 pages.

PCT/US2013/028939, International Preliminary Report on Patentability, dated Jan. 23, 2014, 8 pages.

Power Nap, <en.wikipedia.org/wiki/Power_nap>, Last Modified Sep. 20, 2012, 4 pages.

PowerNap iPhone App, <http://forums.precentral.net/webos-apps-software/223091-my-second-app-powernap-out-app-catalog-nap-timer.html>, Jan. 6, 2010, 10 pages.

Sara_Mednick, <en.wikipedia.org/wiki/Sara_Mednick>, Last Modified Sep. 12, 2012, 2 pages.

Sleep Debt, <en.wikipedia.org/wiki/Sleep_debt>, Last Modified Aug. 25, 2012, 3 pages.

(56) References Cited

OTHER PUBLICATIONS

Sleep Inertia, <en.wikipedia.org/wiki/Sleep_inertia>, Last Modified Sep. 12, 2012, 2 pages.
Sleep, <en.wikipedia.org/wiki/Sleep_stages#Physiology>, Last Modified Oct. 5, 2012, 21 pages.
Slow Wave Sleep, <en.wikipedia.org/wiki/Slow-wave_sleep>, Last Modified Jul. 22, 2012, 4 pages.
Sunseri, Maria, et al, "The SenseWear (TM) Armband as a Sleep Detection Device," <http://sensewear.bodymedia.com/SenseWear-Studies/SW-Whitepapers/The-SenseWear-armband-as-a-Sleep-Detection-Device>, 2005, 9 pages.
Actigraphy, From Wikipedia, the free encyclopedia, downloaded at: http://en.wikipedia.org/wiki/Actigraphy on Apr. 24, 2014, 4 pages.
Desai, Rajiv, The Sleep, Archive for Mar. 2011, Dr. Rajiv Desai Blog, Mar. 17, 2011, 46 pages.
Lichstein, et al., Actigraphy Validation with Insomnia, Sleep, vol. 29, No. 2, 2006, pp. 232-239.
Patel, et al., Validation of Basis Science Advanced Sleep Analysis, Estimation of Sleep Stages and Sleep Duration, Basis Science, San Francisco, CA, Jan. 2014, 6 pages.
Pires, P. D. C. Activity Characterization from Actimetry Sensor Data for Sleep Disorders Diagnosis, Universidade Técnica de Lisboa, Sep. 2008, 10 pages.
Pollak, et al., How Accurately Does Wrist Actigraphy Identify the States of Sleep and Wakefulness?, Actigraphy and Sleep, Sleep, vol. 24, No. 8, 2001, pp. 957-965.
Estimate. (2011). The American Heritage dictionary of the English language (5th ed.). Boston, MA: Houghton Mifflin. Retrieved from <http://search.credoreference.com/content/entry/hmdictenglang/estimate- /0> on Jul. 24, 2017.
Mattila et al., "A Concept for Personal Wellness Management Based on Activity Monitoring," Pervasive Computing Technologies for Healthcare, 2008.
Rechtschaffen et al, "Manual of Standardized Terminology, Techniques and Scoring System for Sleep Stages of Human Subjects." (1968).
Schulz, et al. "Phase shift in the REM sleep rhythm." Pflugers Archiv 358.3 (1975): Abstract.
Schulz, et al. "The REM-NREM sleep cycle: renewal process or periodically driven process?." Sleep 2.3 (1980): 319-328.
Yassouridis, et al. "Modelling and exploring human sleep with event history analysis." Journal of sleep research 8.1 (1999): 25-36.

* cited by examiner

Uses for the Activity Band

Encouraging the user
- coaching for level of activity
- tracking information
- correlating statistics of sleep and activity interaction
- enabling user to perform at his or her best Access Pass
- access to buildings
- access to devices Identification
- color coding
- badge replacement Monitoring
- ergonomics
- sleep patterns
- exercise levels
- all day activity monitoring
- performance sport monitoring Social networking
- visual feedback to everyone regarding user's activity status
- correlated timing for movement or stretching
- automatic uploading of data to competition once initialized

Fig. 10

USER INTERFACE METHODS

-Tactile
- Vibration
- Pulses
- Heat

- Audible
- beeps
- tones
- words
- music
- sounds

- Visual:
-LCD/OLED display
- LED(s)
- patterns
- colors
- e-Ink
- gray scale
- multi-color
- split display with high and low power outputs
- electrochromic polymers (color changing fabric)

Fig. 12

TRACKING AND PROMPTING MOVEMENT AND ACTIVITY

RELATED APPLICATIONS

The present invention claims priority to Utility patent application Ser. No. 14/509,043, filed on October 2014, which claims priority to Utility application Ser. No. 12/819,195, filed on Jun. 19, 2010, which are both incorporated herein in their entirety.

FIELD OF THE INVENTION

The present invention relates to a system to track and prompt user movement and activity utilizing a device designed to be worn.

BACKGROUND

Pedometers have become more popular as a means of monitoring a user's exercise level through-out the day. Many people are active throughout the work day, although they are not actually going to the gym. However, these pedometers are generally inaccurate. Furthermore, it is inconvenient to wear them.

For additional accuracy, more complex activity monitoring systems are provided as well. Some of these devices include accelerometers disposed in the user's shoe, to measure motion more precisely. However, this requires wearing of a special shoe, which is generally not compatible with a work environment.

SUMMARY

An wearable device is described, which tracks and prompts movement and activity. In one embodiment, the device prompts for a sufficient number of units of daily activity, and vigorous activity (e.g. exercise). Movement is designed to ensure that the user moves periodically, during ergonomic activity/inactivity. The units of daily activity tracks and prompts walking or other active behavior during the day. Vigor tracks aerobic activity. These elements are designed monitor the user's activity level. The wearable device comprises an accelerometer, or other motion sensor, to detect motion of a user and an analysis logic to analyze the user's motion.

BRIEF DESCRIPTION OF THE DRAWINGS

The present invention is illustrated by way of example, and not by way of limitation, in the figures of the accompanying drawings and in which like reference numerals refer to similar elements and in which:

FIG. 10 is a chart of one embodiment of the uses of the activity band.

FIG. 12 is a diagram showing one embodiment of the user interface features which may be incorporated into the activity band.

DETAILED DESCRIPTION

The method and apparatus described includes an activity band designed to be worn by a user throughout the day. The activity band, in one embodiment, is designed to be worn throughout the day and the night. This enables the activity band to monitor the user's motion during the day as well as while sleeping. The tracking of sleeping using actigraphy enables the detection of sleep phases and circadian rhythms using a simple activity band worn on the wrist. In one embodiment, the sleep monitoring may include detecting one or more of: insomnia, circadian rhythm sleep disorders, excessive sleepiness and restless legs syndrome. It can also be used to determine the results of various sleeping patterns. In one embodiment, the data obtained by the activity band may be used to track the user's activity level, create correlations between behaviors, and/or track various other health-related features, such as ergonomics, eating patterns, etc.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1A:
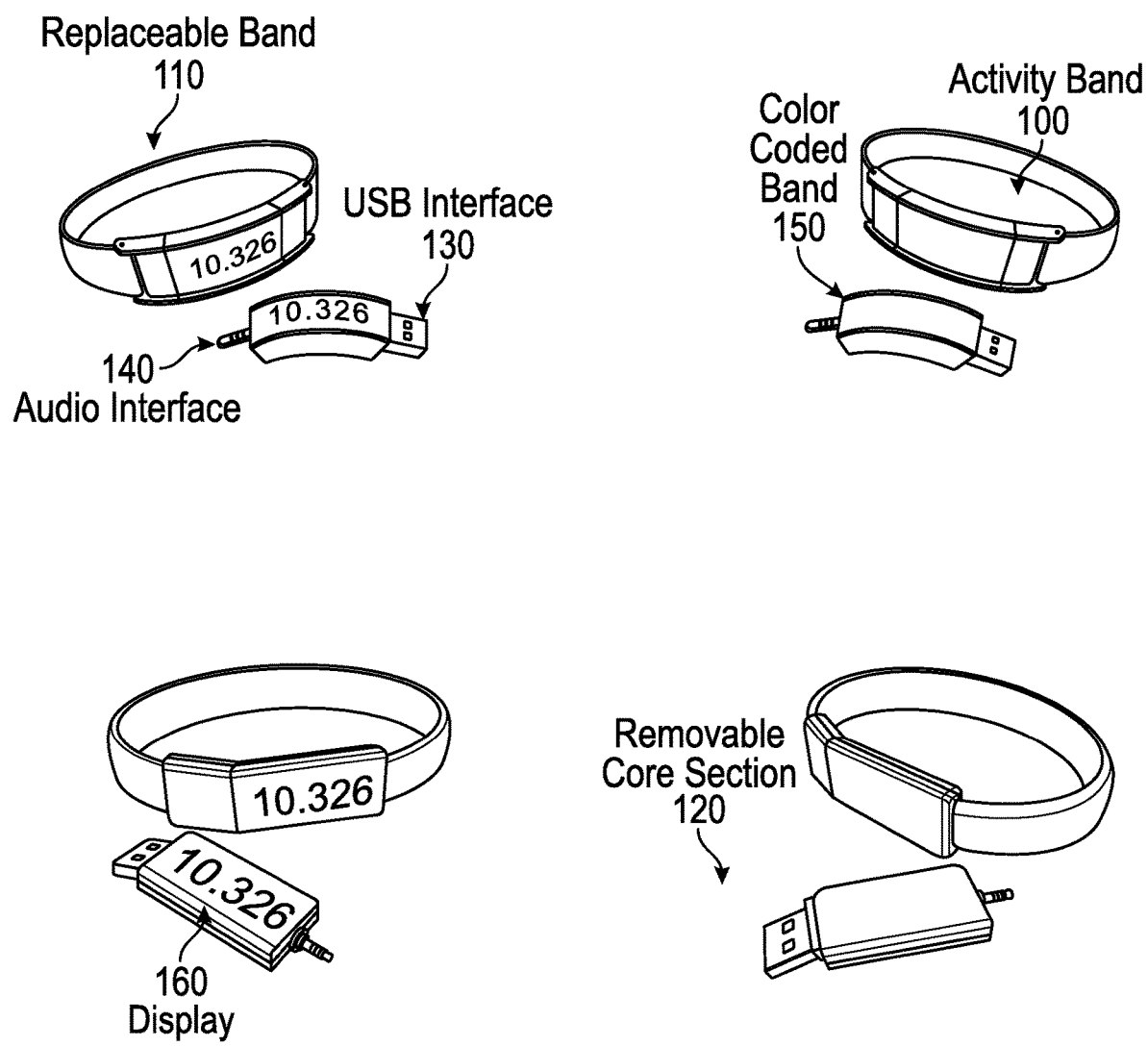
FIG. 1A illustrates exemplary configurations of an activity band.

FIG. 1A illustrates exemplary configurations of an activity band. The activity band 100 in one embodiment is water-proof or water-resistant, and designed to be worn throughout the day and night. The activity band 100 in one embodiment includes a removable core section 120 coupled to a replaceable band 110. The replaceable band 110 is designed, in one embodiment, to be a fashion accessory, which can range from leather, or imitation leather, to crystal-decorated or rubbery materials. The replaceable band 110 may be made of any material, in general.

The removable core section 120 contains, in one embodiment, the sensors and processors which are part of the activity band. In one embodiment, the core section 120 has at least one connector. In one embodiment, the connector is a Universal Serial Bus (USB) format connector 130. In one embodiment, the USB format may be Type A, Type B, mini-A, Mini-B, Micro-B, Micro-AB, or another format now used or developed in the future. In one embodiment, the connector is an audio interface 140, which enables the activity band 100 to be coupled to a mobile device via a headphone jack. This enables connection to mobile devices which do not have a USB. Alternative connectors may be used.

In one embodiment, the core section 120 or another part of the activity band may be a color coded band 150. The color-coded band 150 may show an "overall health status" in a visual way that is easy to share with others. In one embodiment, the removable core section 120 may have a display 160 which may show activity level to the user. The activity level may be the number of steps, a performance compared to the user's set goals, etc. This display 155 may be active only during exercise, upon request, continuously, periodically, or sporadically based on another setting. The color-coded band 150 or display 155 may coexist. In one embodiment, the display may be an LCD (liquid crystal display), OLED (organic liquid crystal display), electronic paper, or alternative format. In one embodiment, the display may be part of the replaceable band 110, in a format that enables displays to be integrated into the band itself.

Figure 1B:
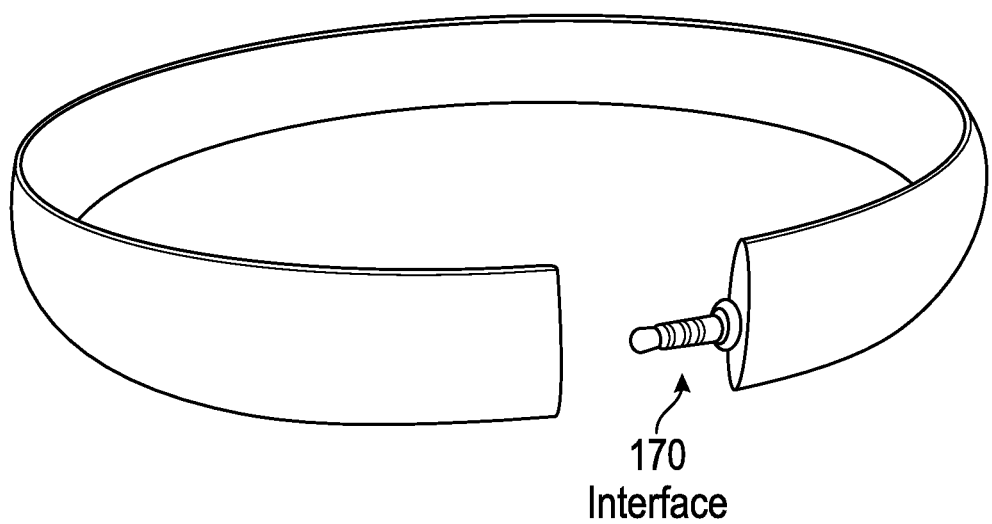
FIG. 1B is a view of an alternative embodiment of an activity band.
Figure 1C:
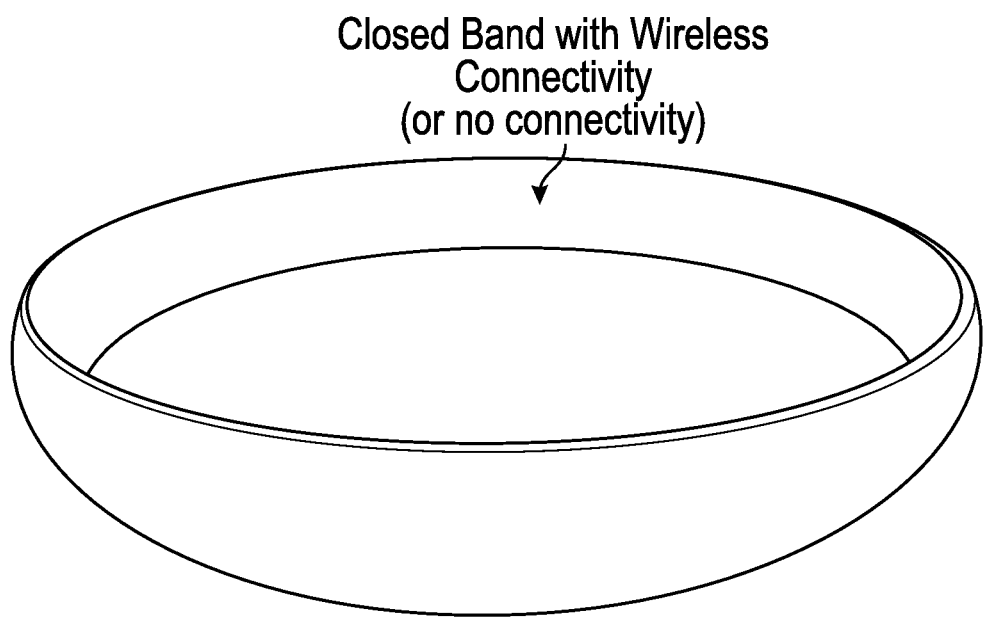
FIG. 1C is a view of an alternative embodiment of an activity band.

In one embodiment, instead of having a separable core part 120 and a band 110, the system is integrated into a single piece 160, as shown in FIG. 1B. In one embodiment, the single piece may come apart at a connector point, which may reveal one or two connectors 170 as shown in FIG. 1B. Alternatively, the activity band may be a single unitary piece as shown in FIG. 1C. In one embodiment, such a unitary activity band may communicate via a wireless or contact-based system. Alternative configurations of the activity band may be utilized.

Figure 2A:
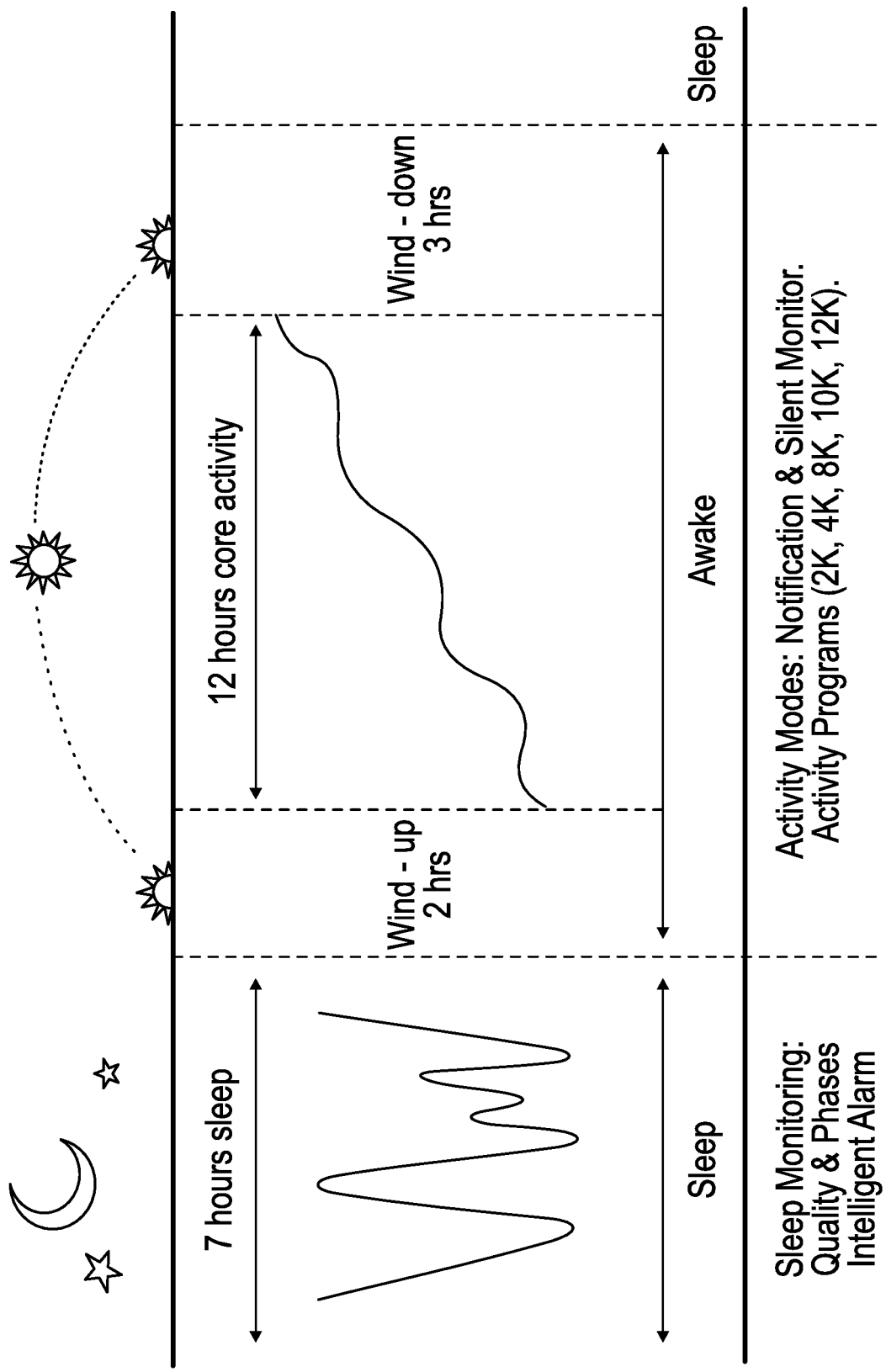
FIGS. 2A-B are diagrams of embodiments of the display of data gathered by the activity band.
Figure 2B:
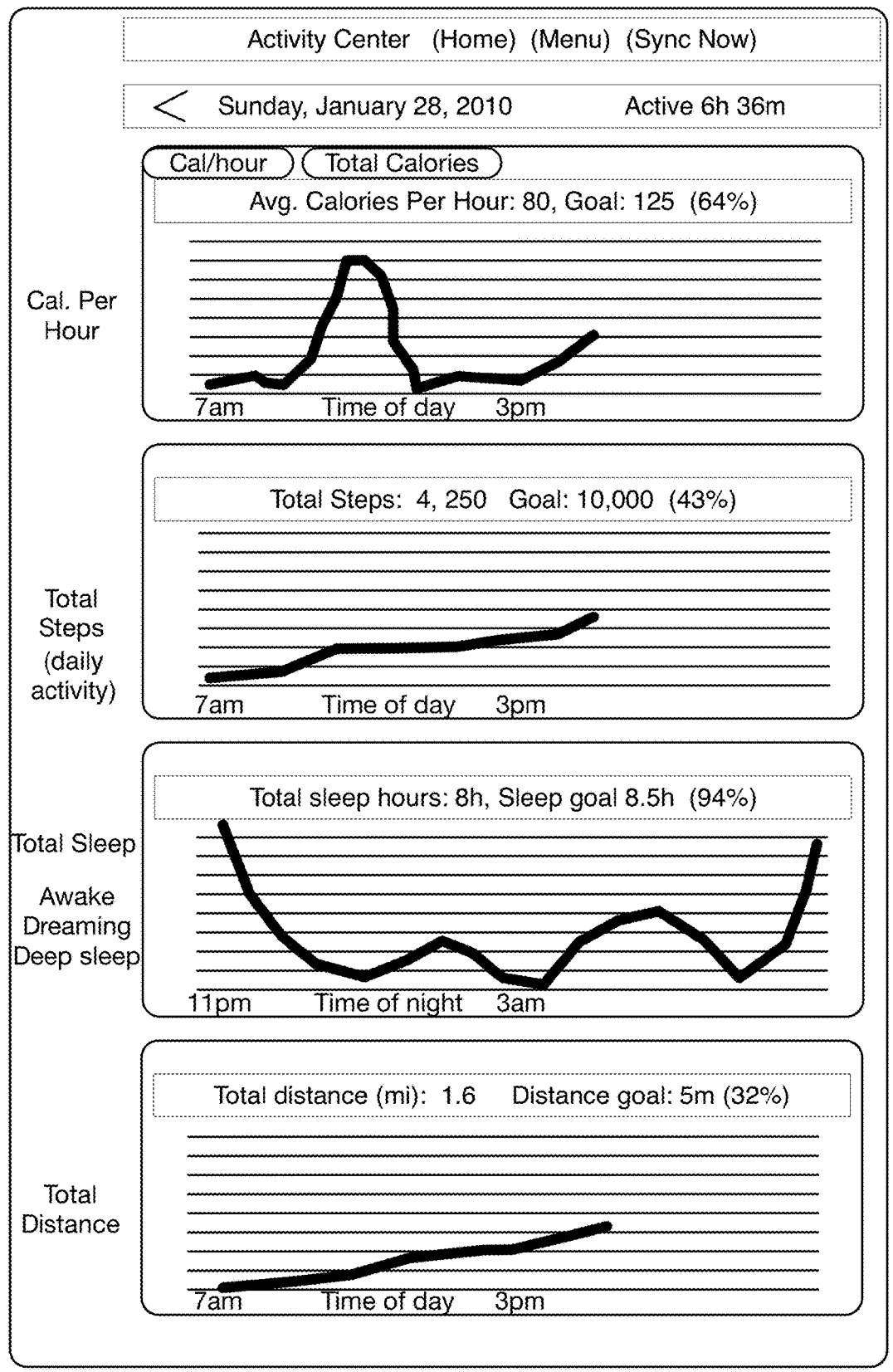

FIGS. 2A-B are diagrams of embodiments of the display of data gathered by the activity band. FIG. 2A illustrates one embodiment of the types of data that the activity band can track. It can track sleep, including the various stages of sleep, as well as activity, and the various activity levels. In one embodiment, activity types can also be tracked. In one embodiment, the wind-up and wind-down times may be times when the user is not wearing the activity band. In another embodiment, the user may wear the band 24 hours a day, in which case no such period may be shown.

FIG. 2B is a diagram of one embodiment of the data displayed to the user. In one embodiment, the various selections shown may be chosen by the user. In one embodiment, this interface may be shown on a computer, such as a web page provided by a server, a user's own computer, or a handheld device. In one embodiment, each of these displays corresponds to a screen available on the user's handheld device. In this example, the system shows calorie consumption per hour, which indicates the level of activity as well.

The exemplary display also shows the number of steps taken per hour, and separately the distance traveled. The steps taken can be referred to as Units of daily activity. In one embodiment, in addition to tracking the number of steps, other types of exercise motions may also be separately tracked, or tracked in the same graph. This can be referred to as Vigor or "vigorous activity." For example, if the user bicycles, uses an elliptical machine, or uses another exercise apparatus or mode of human powered travel, the motions associated with those types of exercise may also be shown. One example of how such data is derived is shown in U.S. patent application Ser. No. 12/069,267, entitled HUMAN ACTIVITY MONITORING DEVICE WITH ACTIVITY IDENTIFICATION, assigned to the assignee of the present invention, and incorporated herein by reference.

The system also may show, in one embodiment, the sleep patterns of the user using actigraphy, in one embodiment. The sleep patterns may separate the sleep into various phases, such as dreaming, deep sleep, transition, etc. In one embodiment, the patterns may be updated based on current scientific knowledge. However, the information is generally derived from the user's unconscious motions during sleep. In one embodiment, other aspects (e.g. heart rate, breathing patterns, etc.) may also be monitored and used as part of the sleep cycle determination.

Figure 3:
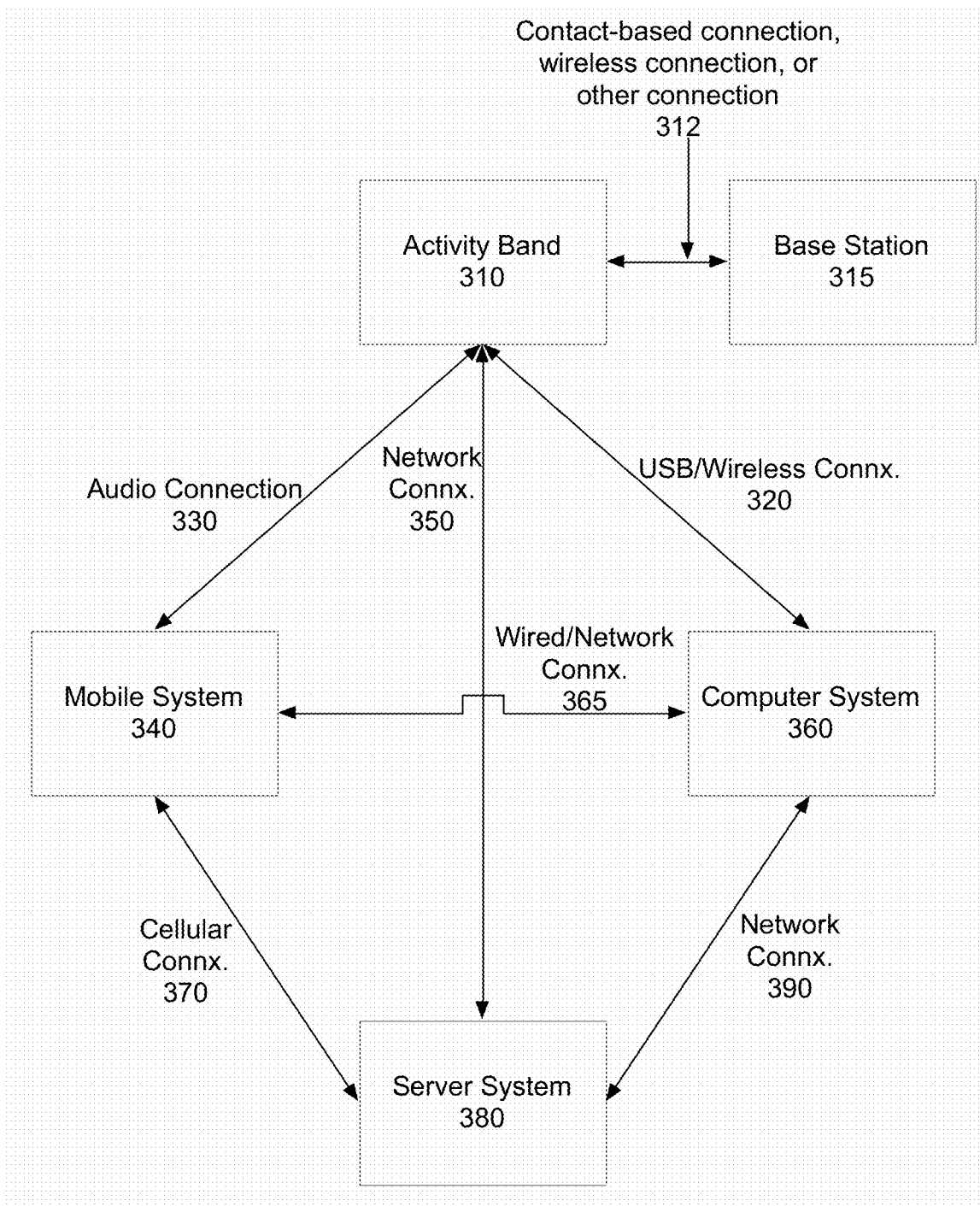
FIG. 3 is a diagram showing communication between the activity band and a plurality of devices.

FIG. 3 is a diagram showing communication between the activity band and a plurality of devices. The activity band 310 may have one or more forms of interfacing with other devices. In one embodiment, the activity band may be self-contained, and have no interfaces. However, in most embodiments, the activity band 310 would include at least one interface.

The interface, in one embodiment, may be to a mobile system 340, a computer system 360, and/or a server system 380. The activity band 310 may have different formats for connecting with various devices. The types of connection may include a USB connection or wireless connection 320 to a computer system 360, an audio connection 330 to a mobile system 340, network connection 350 to a server system 380, and a contact-based connection, wireless connection, or another type of connection 312 to a base station 315. In one embodiment, the activity band 310 may include a USB-type interface to enable USB connections, and an audio interface to enable audio connections. The activity band 310 may further include a network connection, e.g. wireless networking, cellular network (CDMA (Code Division Multiple Access), TDMA (Time Division Multiple Access), 3G (Third Generation), etc.), personal area network such as BLUETOOTH™, or other non-physical connection, which enables the activity band 310 to communicate with computing devices of various sorts (e.g. mobile devices, desktop devices, server devices.) The communication, in one embodiment, may include the activity band sending its data to a device to enable the user to have a richer user experience. The communication, in one embodiment, may include the sending of preferences to the activity band 310. Other types of communication may also take place.

As shown in FIG. 3, the various communication modes may be used with different computing devices. However, in one embodiment, the activity band 310 may use multiple modes of communication with a single device.

In one embodiment, the activity band 310 may interface with a base station 315, which in turn may be coupled to one or more other devices such as mobile system 340, computer system 360, or server system 380. The base station 315 may connect to the activity band 310 through a wired connection, contact-based connection, wireless connection, or other means. The use of the base station 315 enables simpler activity band 310, while still permitting connection to various devices.

In one embodiment, the activity band 310 may be charged through a USB connection. In one embodiment, the activity band 310 may be charged through inductive charging, using base station 315. In one embodiment, the activity band may be charged through a wireless signal or another non-contact based power transmission. In one embodiment, the activity band 310 may be charged by the user's motion in a kinetic manner. In one embodiment, the activity band 310 may be charged via solar charging. In one embodiment, the activity band 310 may use replaceable batteries, and may not need charging capability. Alternative methods of providing power to the activity band may be used.

Figure 4A:
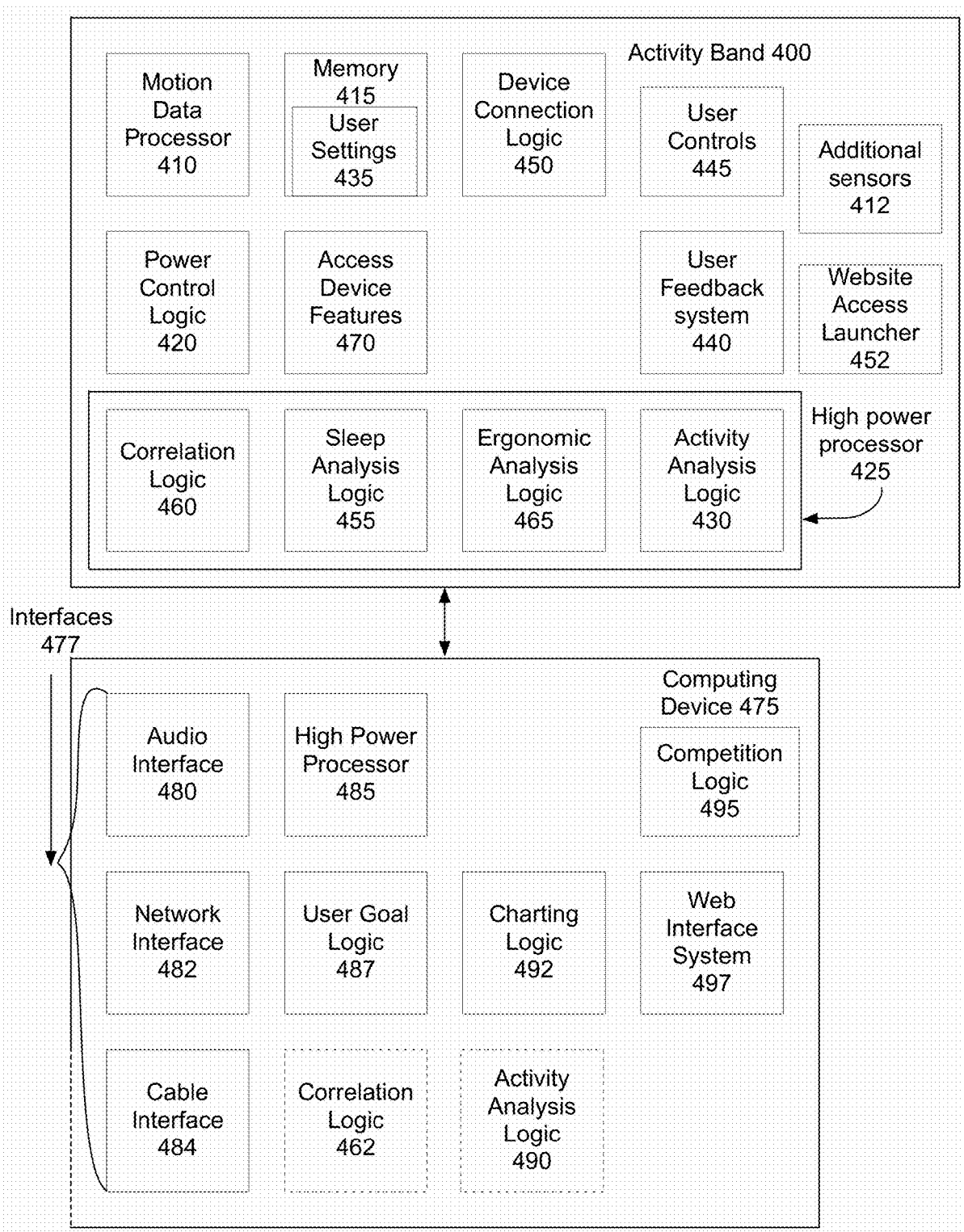
FIG. 4A is a block diagram of one embodiment of the activity band and a computer system to which the activity band is coupled.

FIG. 4A is a block diagram of one embodiment of the activity band and a computer system to which the activity band is coupled. The activity band 400 in one embodiment includes device connection logic 450 to couple the activity band to one or more computing devices 475, through one or more connection mechanisms. These connection mechanisms may include one or more of wired connections such as an audio interface or USB interface, wireless connections such as wireless network connection (WIFI) and personal area network (BLUETOOTH), contact-based connections, or other types of connections.

In one embodiment, if the activity band 400 is coupled to a computing device, website access launcher 452 may automatically start a browser application on the computing device. This browser would have an automatic URI (universal resource indicator), which would provide access to a server device. In one embodiment, the access connection is secure. In one embodiment, the activity band 400 logs into the server, to enable the server to present the user's personal data on the computing device. This enables the activity band 400 to be coupled the server through any intermediary device (e.g. mobile device, local computer, etc.) without requiring the installation of any software on the local device. In one embodiment, no data is stored on the local device, so that the user's private data is not available once the activity band is disconnected, and the web site is closed. In one embodiment, when the activity band is disconnected, the browser window associated with the user's activity data is automatically closed by website access launcher 452.

Activity band includes motion data processor 410, which may in one embodiment include a motion system such as an accelerometer. The accelerometer may be may one or more three-dimensional, two-dimensional, or one-dimensional accelerometers. In one embodiment, the motion sensor may be a gyroscope, or an accelerometer combined with a gyroscope. In another embodiment, an alternative motion sensing mechanism may be used.

In one embodiment, the activity band may include additional sensors 412. Such additional sensors may include one or more of: a GPS receiver, a barometer, a magnetometer, a heart rate monitor, a blood pressure monitor, a blood oxygenation monitor, or other sensors. The data from these sensors may be used to refine analysis and detection, or provide additional data.

In one embodiment, memory 415 is used to temporarily store data, and store user statistical data. Memory may be a random access memory, a flash memory, or alternative storage media.

User settings 435 store user preferences. The user preferences may be entered through user controls 445, in one embodiment. In one embodiment, the user control on the activity band 400 may be simply an on-off switch. In one embodiment, the on-off switch turns off user communication but does not turn off the motion system itself. In another embodiment, the user can turn off the activity band entirely. In one embodiment, the user preferences may be entered at a computing device 475 and may be passed to the activity band 400 via device connection logic 450, and stored in memory 415.

In one embodiment the activity band includes power control logic 420. Power control logic 420 controls the motion data processor 410, as well as the high power processor 425 which provides the analysis and correlation logics, in one embodiment. In another embodiment, the analysis and correlation logics may be in computing device 475. The power control logic 420 is designed to improve battery life by reducing power consumption. By turning off those aspects of the system that are not needed, the system can conserve power. In one embodiment, the motion data processor 410 and memory 415 are powered continuously when the activity band is on, while the remaining parts of the activity band are powered only when needed.

The activity band 400 may in one embodiment include access device features 470 which enable the activity band 400 to be used as an access device. The access device features 470 may be an RFID-based system, magnetic strip, or another system that enables programming of the activity band 400 with a particular identity for access to locations, devices, etc. This enables the activity band to be used as a replacement for a badge, or similar access key. In one embodiment, the activity band may also be printed with an image of the user, the name of the company, or similar data to provide the same features as a traditional access badge.

User feedback system 440 may include an audio output (e.g. speaker), tactile feedback (e.g. small motor to provide movements such as vibrations or poking), visual output (liquid crystal display (LCD) screen, electronic paper, one or more light emitting diodes (LEDs), or other visual output mechanisms). The user feedback system provides information to the user about, in one embodiment, the current status of the activity band, user's activity level, warnings, and other relevant information. The user feedback system 440 may be controlled by power control logic 420. In one embodiment, the user feedback system may be related to feedback on activity levels, behaviors, sleep levels, etc. In one embodiment, user feedback system 440 also includes information provided to the user that is unrelated to the motion data, e.g. time, temperature, or other sensor data, or other information.

The high power processor 425 may be part of the activity band 400. The high power processor 425 in one embodiment includes activity analysis logic 430. Activity analysis logic 430 analyzes the user's current activity level, and compares it to the user settings 435. If the activity level is below the user's preferences, the user feedback system 440 may be activated by the activity analysis logic 430. This may be used to prompt the user, to reach his or her activity goals. In one embodiment, the high power processor 425 is only activated by power control logic 420 at the appropriate time to perform the analysis.

Ergonomic analysis logic 465 analyzes the user's motion for compliance with ergonomic standards, which may be stored as user settings 435, in memory 415. If the user's activity is against the ergonomic guidelines, the ergonomic analysis logic 465 may activate the user feedback system 440. The user may be prompted to move, if the user's activity is against the guidelines. This can be referred to as Movement, as lack of motion over an extended period is a health risk.

Sleep analysis logic 455 is used to enable the activity band 400 to act as an alarm clock. The sleep analysis logic 455 uses the programmed in waking time, from user settings 435, and the motion data to determine an appropriate time to wake the user.

Correlation logic 460 correlates the user's activity levels, sleep, and other observed behaviors to determine what behaviors result in a better result for the user. The correlation may be for quality of sleep or insomnia (e.g. correlate activity level, sport performance, activity and sport timing, and potentially other data with quality of sleep), performance level at a sport with overall activity level and/or sleep, etc. Correlation logic 460 may correlate all available sets of data. In one embodiment, a neural network based learning system may be used. In another embodiment, a simple correlation system may be used in which initial correlation assumptions are strengthened and weakened based on observed user data.

In one embodiment, correlation logic 460 may be on the remote computing device. In one embodiment, correlation logics 460, 462 may be on both the activity band 400 and computing device 475. In one embodiment, processing may be distributed between the two devices. In another embodiment, preliminary correlation may be established by the correlation logic 460 on the activity band 400, while more complex correlations are established by the computing device 475. In one embodiment, the computing device 475 may include a local device, such as a mobile phone, and a remote device such a server which receives data from the local device. In one embodiment, any of the elements described as being associated with the computing device may be split between various devices that may receive data, directly or indirectly, from the activity band.

The computing device 475 includes in one embodiment one or more device interfaces 477. The device interfaces 477 may include one or more of an audio interface 480, network interface 482, and cable interface 484 (USB cable, or other cable format). The activity band 400 communicates its data to the computing device 475, and receives its data, via the device interfaces 477. In one embodiment, the connection between the activity band 400 and the computing device 475 may be indirect, through a dock, or intermediary device. The intermediary device may be another computing device (e.g. a mobile system) or a special purpose device (e.g. a docking station), or another type of device that can be coupled to the activity band 400 and used to provide data to computing device 475.

In one embodiment, the computing device 475 includes charting logic 492, to enable the user to see a visual representation of the activity and motion levels. FIGS. 2A and 2B show exemplary charts that may be generated by charting logic 492.

In one embodiment, the computing device 475 includes a correlation logic 462 and activity analysis logic 490. In another embodiment, the data for this is received directly from the activity band and no such logics are included in the computing device 475.

User goal logic 487 enables the computing device to provide the benefit of setting goals for activity levels, ergonomic levels, weight loss levels, sleep levels, etc. This data is used to calculate the user settings for activity levels, ergonomics, and sleep which are used by activity band 400. Activity levels may include a level of Daily Activity, such as steps taken per day, as well as a level of Vigorous Activity, such as exercise.

Web interface system 497 in one embodiment enables the computing device 475 to post the user's activity levels to various social networking sites, as specified by the user's preferences. Competition logic 495 enables the system to provide a virtual competition between users.

In one embodiment, computing device 475 is a server, and connects to the activity band 400 via an intermediary device, such as a personal computer. In another embodiment, the computing device 475 is a personal computer, a mobile device, or a docking station or similar special-purpose device.

Figure 4B:
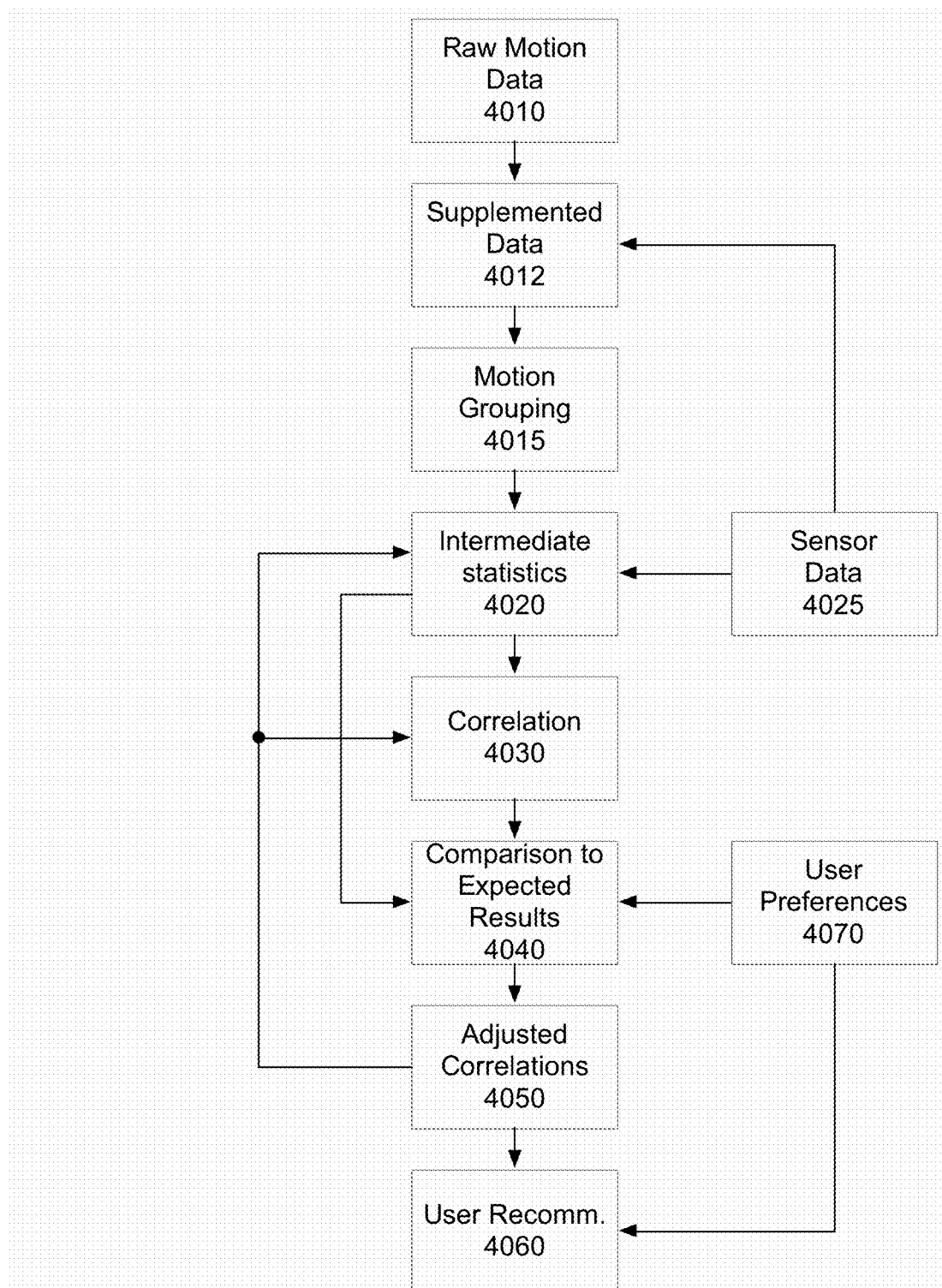
FIG. 4B is a block diagram of one embodiment of the correlation logic.

FIG. 4B is a block diagram of one embodiment of the correlation logic 460. The raw motion data is received, in one embodiment from accelerometer device or other motion sensor. In one embodiment, the raw motion data 4010 is supplemented by data from other sensors to generate supplemented data 4012. Such sensor data 4025 may include gyroscopes, GPS sensors, barometers, compasses, thermometers, and any other sensors which may be available within the activity band or from outside sources. In one embodiment, for example, the local temperature and/or humidity may be obtained from government weather tracking data or other information. Thus, in some instances the additional sensor data 4025 may not be obtained from activity band.

The supplemented data 4012 is then grouped in one embodiment, to provide motion grouping data 4015. Motion grouping data 4015 groups motions associated with a particular activity. For example, motions associated with "sleeping" are grouped for evaluation. Similarly, motions associated with various activities (e.g. walking (daily activity), jogging, using an exercise machine, bicycling (vigorous activity), typing or other ergonomic activity (movement activity), etc.) is grouped in one embodiment.

The grouped data is used to generate intermediate statistics 4020. The intermediate statistics 4020 may be adjusted based on sensor data 4025. For example, the activity intensity may be adjusted based on the temperature, or the incline travelled.

The intermediate statistics 4020 are used to generate the correlation 4030. The correlation 4030 describes the relationship between various statistical levels. For example, the correlation may be as follows:

| Sleep Level | Activity Level (Units of daily activity) | Sport Performance (Vigorous Activity) | Ergonomics (Movement) |
|---|---|---|---|
| Goal: Good | Moderate | Low | High |
| Good | Goal: High | High | Moderate |
| Excellent | Moderate/Low | Goal: High | Moderate |

Thus, for example, for high sports performance goal, the user needs excellent sleep, moderate to low other exercise, and moderate ergonomic level. In one embodiment, there is a default set of assumptions for the correlation. Each correlation is then strengthened or weakened based on observed data.

The correlation 4030 is compared to expected results 4040. In one embodiment, the user preferences 4070 as to goals.

The correlations are adjusted based on the comparison, to produce adjusted correlations 4050. The adjusted correlations 4050 are used to generate the intermediate statistics 4020, and correlation/comparison 4030.

The adjusted correlations and statistics are used to provide user recommendations 4060, in one embodiment. The user recommendations depend on the user preferences 4070, and the observed correlations. The user preferences 4070 in this case may include the user's goal (e.g. better sleep, better ergonomics, better activity level, better sports performance, etc.).

The resulting user recommendations 4060 may be used by the activity band to suggest activity/actions to the user. For example, if the user wishes to get better quality sleep, and the correlation has determined that moderate exercise an hour before bed increases sleep quality, the user may be prompted to perform such activities. Similarly, the user may be prompted to move, perform daily activities, and perform vigorous activities.

Figure 5:
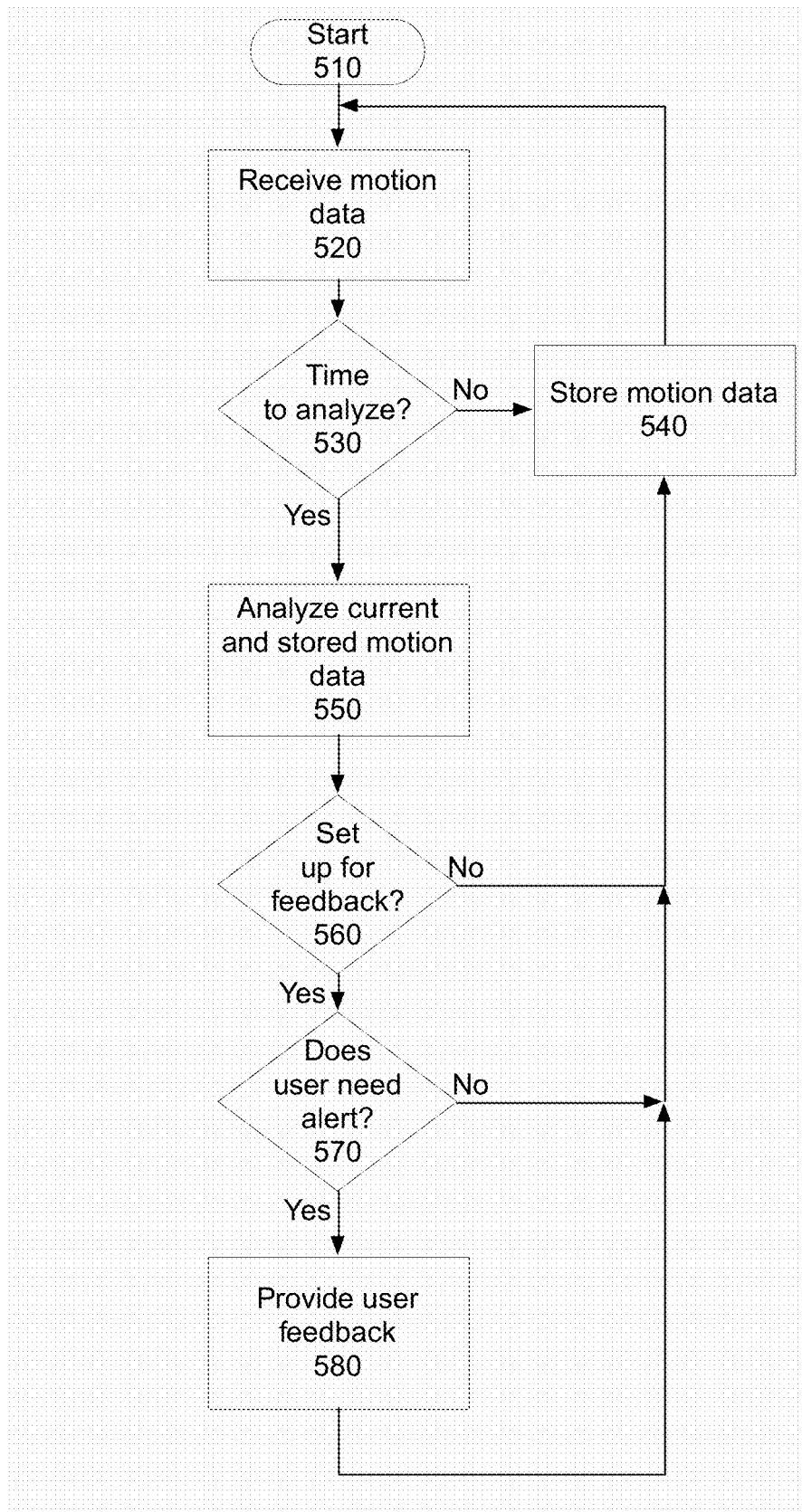
FIG. 5 is an overview flowchart of one embodiment of the activity band use.

FIG. 5 is an overview flowchart of one embodiment of the activity band use. The process starts at block 510. In one embodiment, whenever the activity band is in use (e.g. worn by a user, and not turned off) this process is active. In one embodiment, the user may activate this process, or deactivate it.

At block 520, the activity band receives motion data. The motion data may be from one or more accelerometers, gyroscopes, other devices for monitoring motion data.

At block 530, the process determines whether it is time to analyze the data. In one embodiment, the time to analyze the data is determined based on an amount of data collected. In one embodiment, the time to analyze the data is determined based on when the activity band successfully establishes a connection with a computing device, enabling the processing to take place on the computing device, or to be shared between the activity band and the processing device. In one embodiment, when the user switches between activity types, the time to analyze is triggered.

If it is not yet time to analyze the data, the data is stored at block 540, and the process continues to receive motion data. In one embodiment, although this is illustrated as a flowchart, the process is actually interrupt driven, and when either a timer indicates that it is time to analyze the data, a connection is established, or some other occurrence triggers analysis, the analysis process is woken up to analyze the stored motion data. Meanwhile, the motion data is continuously received and stored independently of the analysis.

If it is time to trigger the analysis, at block 550 the stored motion data and current motion data is analyzed. In another embodiment, only stored motion data is analyzed. In another embodiment, the analysis takes place continuously and only current motion data is analyzed, in conjunction with the results of prior analysis.

At block 560, the process determines whether the activity band is set up to provide feedback to the user. The feedback may be audio, visual, tactile, or another type of feedback that would provide information about the results of the analysis to the user. If the system is not set up for feedback, the process continues to block 540, where the motion data (in one embodiment the raw and processed motion data) is stored, and the process returns to continue monitoring motion data, at block 520.

If the system is set up for feedback, the process at block 570 determines whether the user information should be updated. In one embodiment, this may depend on the type(s) of user feedback available as well as the user's preferences. For example, some users may set their preferences to only be alerted if their activity is harmful, or if a change in activity is needed to achieve a user goal. Other users may wish to receive information about their progress more regularly. In some embodiments, the user feedback may be visual and low impact (e.g. updating the step count shown on the activity band, or the color code reflecting the user's activity level). If the user does not need an alert, based on the analyzed data, the user preferences, and/or the available feedback mechanisms, the process returns to block 540 to store the motion data, and in one embodiment, the processed motion data.

If the user feedback should be sent, the process provides the user feedback at block 580. This user feedback may include verbal instructions, music, tones, LED lights or flashes, changes in color displays, text or other display, vibrations, etc. The process then returns to block 540 to store the raw and/or processed motion data.

Figure 6:
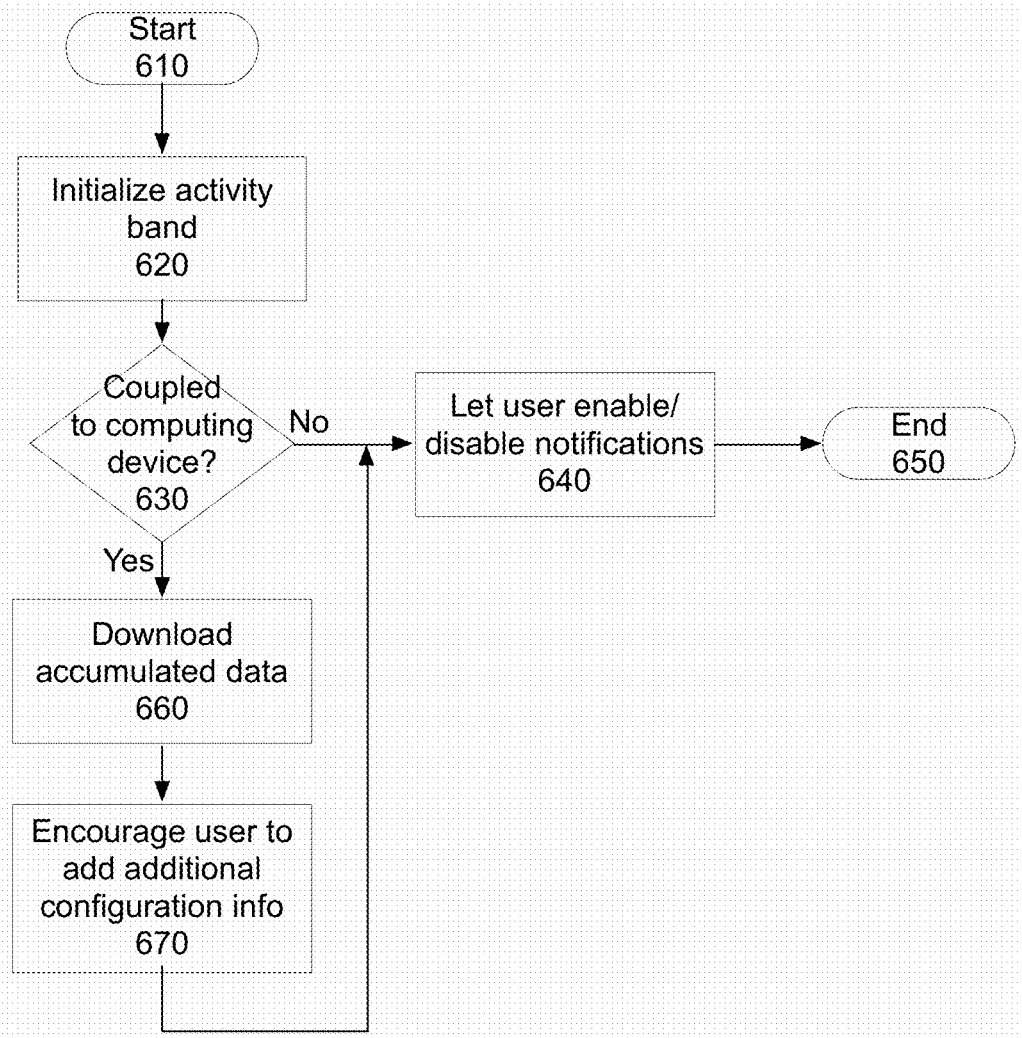
FIG. 6 is a flowchart of one embodiment of configuring settings for the activity band.

FIG. 6 is a flowchart of one embodiment of configuring settings for the activity band. In one embodiment, this configuration may take place the first time the user interacts with the activity band. In one embodiment, all or a portion of this configuration may take place every time the user activates the activity band.

At block 620, the activity band is initialized. In one embodiment, if this is the first time the activity band has been turned on, the initialization may upload/retrieve/activate default settings to the activity band. The default settings may be altered at any time by the user in one embodiment.

At block 630, the process determines whether the activity band is coupled to a computing device. The computing device may be a local laptop, desktop, net book, or other computer, a remote computer or server, or a mobile device such as a mobile phone including processing capability, or a personal digital device. If the activity band is coupled to a computing device, the process continues to block 660.

At block 660, the accumulated data is downloaded from the activity band, if there is stored data.

At block 670, the user is enabled to add additional configuration data to the activity band. In one embodiment, the system automatically displays a request to enter personal data and/or configuration data when the application associated with the activity band is enabled. In one embodiment, a software application may be run on the computing device. In another embodiment, the computing device may connect to a web site and no application may reside on the system. In one embodiment, the activity band may launch a browser to connect to a server, on which the data is hosted. However, from the perspective of the user, the interface is similar, in one embodiment.

The process then continues to block 640, to let the user enable/disable notifications. In one embodiment, the user may set notifications on the action band, which are given to the user during wear. The format of the notification may include one or more of audio, tactile, and visual notification through the activity band itself. In one embodiment, the activity band may also deliver its notifications to another device through a wireless connection. In one embodiment, the activity band may communicate to the user via email, SMS or a similar messaging feature in which messages are displayed on a related device such as a user mobile device.

The process ends when the activity band is disconnected from the device, in one embodiment. In another embodiment, if the connection is a wireless connection the process may end when the user is out of range, or when the activity band stops sending data to be downloaded.

In one embodiment, the activity band is turned on and then is not coupled to a computing device, as determined at block 630. In that instance, the process continues directly to block 640, to enable the user to turn on and off notifications. In one embodiment, the user may also set other preferences and settings through the activity band. In one embodiment, however, the activity band has a simple interface and thus no complex interface settings may be made without connection to the computing device. In another embodiment, the activity band may include an interface that enables complicated settings.

Figure 7:
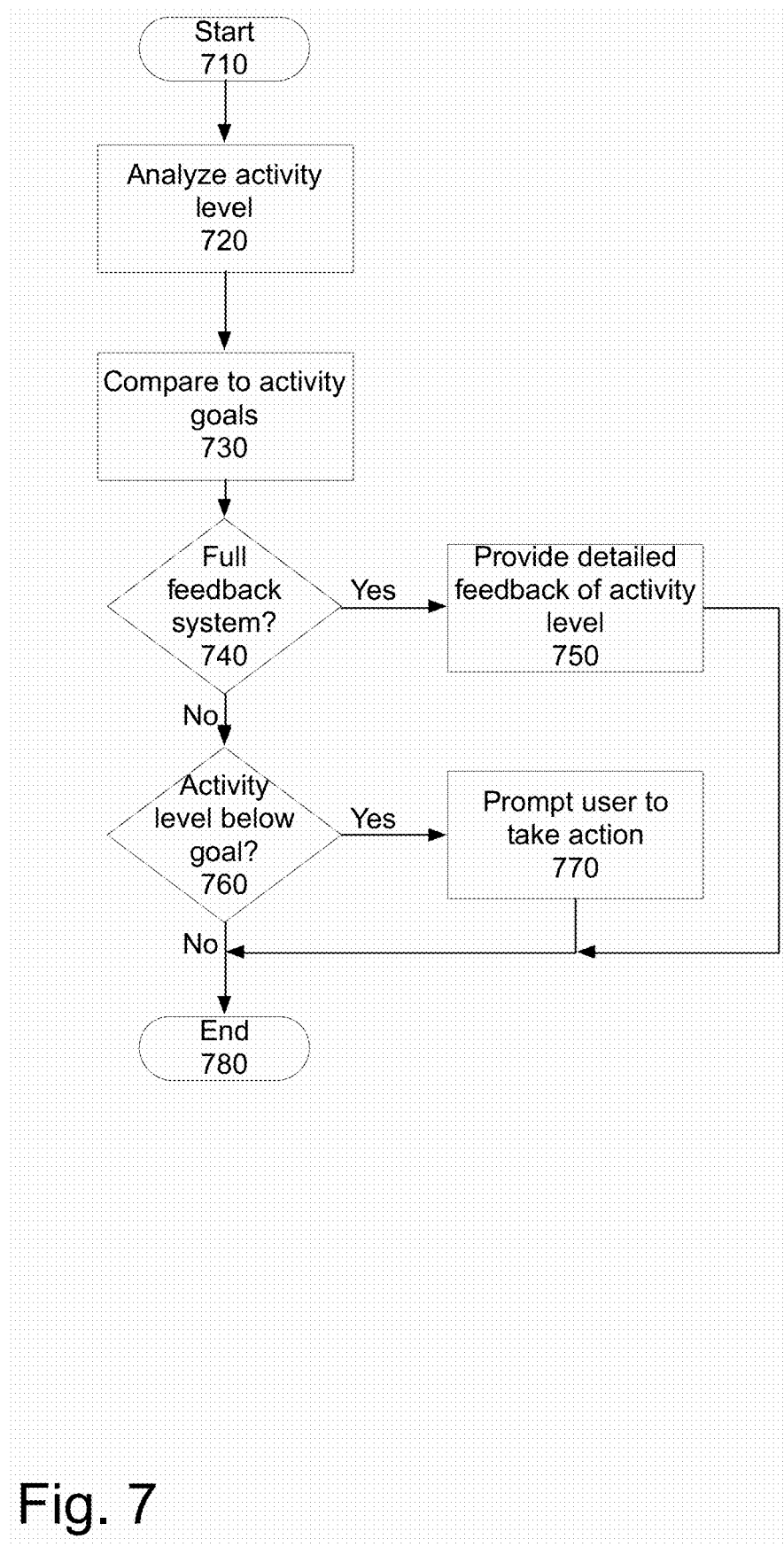
FIG. 7 is a flowchart of one embodiment of using the activity band to ensure a healthy level of activity.

FIG. 7 is a flowchart of one embodiment of using the activity band to ensure a healthy level of activity. This may include a level of daily activity and a level of vigorous activity. In one embodiment, this goal may be identified by the user. In one embodiment, this may be a default goal provided with the system, but may be removed or altered by the user. The process starts at block 710. In one embodiment, this process is initialized, as shown in FIG. 5, when it is time to analyze data. In one embodiment, the data analysis occurs periodically. In one embodiment, the timing may depend on the user preferences. For example, in one embodiment, a user may set only a total daily activity goal. In that case, the analysis may be done three or four times a day, or less frequently. By contrast, if a user has an hourly activity goal, the analysis may be done much more frequently. In one embodiment, the frequency of the analysis may also depend on the results of prior analysis. For example, in one embodiment, if the user is far from his or her goal, the analysis may occur more frequently, to ensure that the user has sufficient time to reach the goal activity level. In one embodiment, the analysis may be done when the user's activity level changes, e.g. from moderately active to inactive or vice versa.

At block 720, the activity level is analyzed. The activity level may include a step count, in one embodiment. The activity level, in one embodiment, may be a combination of distance travelled, steps taken, and types of activities counted.

At block 730, the calculated daily activity levels are compared to the daily activity goals. For example, the user may set goals such as:

walk a minimum of 4 miles (daily activity),
take a minimum of 10,000 steps (daily activity),
ride at least 10 miles on a bicycle (vigorous activity),
use an elliptical machine for at least 2 miles (vigorous activity),
ride at least 5 miles on a bicycle and walk at least 1 mile (vigorous activity and daily activity),
consume at least 500 calories with activity,
another format of activity level evaluation,
a combination or alternatives selected from of two or more of the above types of activities.

In one embodiment, in order to set a calorie based goal, the user is asked to enter additional data such as bodyweight, height, etc. In one embodiment, calorie based goals may also take into account other factors such as incline associated with walking, temperature and humidity associated with activity, etc.

At block 740, the process determines whether there is a full feedback system. If there is a full feedback system, the process continues to block 750. At block 750, the detailed feedback is provided. In one embodiment, the detailed feedback is provided via a color code displayed on the activity band. In another embodiment, the detailed feedback may be provided via a message sent wirelessly to an identified device. In another embodiment, the detailed feedback may be provided on a screen, via a speaker, or through another mechanism. The process then ends, at block 780.

If there is not a full feedback system, as determined at block 740, the process continues to block 760. At block 760, the process determines whether the activity level is below the goal. If so, the process continues to block 770. At block 770, feedback is provided to the user indicating that the user is below the expected level of activity. This feedback may be audio feedback (e.g. a beep, a voice announcement, a tone, a musical indicator, etc.), visual feedback (e.g. LEDs lighting up or blinking in a particular pattern), tactile (buzzing, vibration, or other tactile indicator), or another type of indicator. In one embodiment, based on user preferences, a message may be sent wirelessly to another device (e.g. the user's phone, or email). The process then ends, at block 780. This type of coaching, to enable the user to stay on track with their goals encourages healthy behavior.

Figure 8:
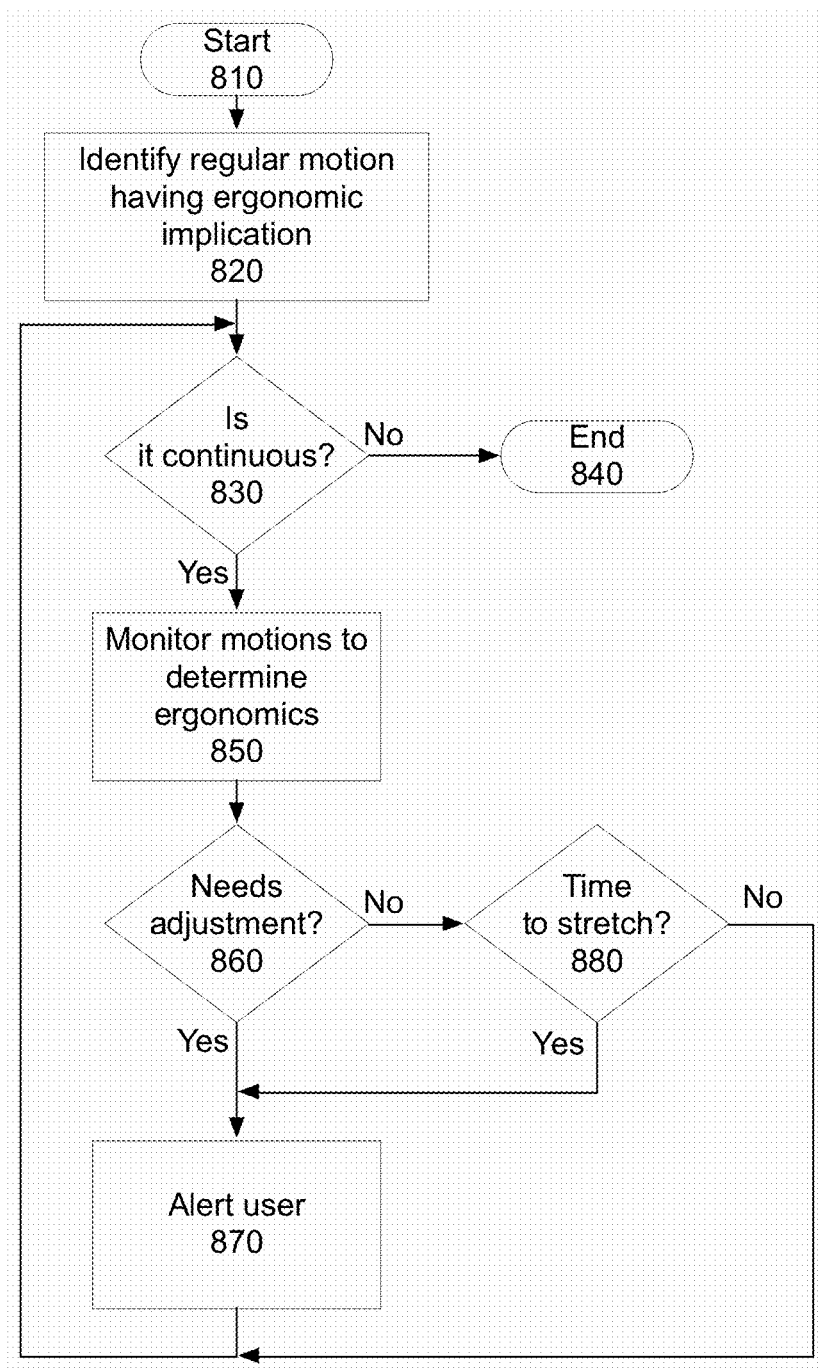
FIG. 8 is a flowchart of one embodiment of using the activity band to ensure ergonomic behavior.

FIG. 8 is a flowchart of one embodiment of using the activity band to ensure ergonomic behavior. One of the possible uses of the activity band is to monitor ergonomics. Ergonomics include in some embodiments, one or more of typing form (e.g. wrist and hand positioning while typing), stretching, posture, and other data which can be derived from motion data. Ergonomics in one embodiment includes immobility, e.g. lack of movement over an extended period while awake. In one embodiment, a user or an enterprise may set the ergonomic principles to monitor into the activity band. The specific examples given here are focused on typing. However, one of skill in the art would understand that other types of repetitive motion and other types of ergonomic standards may be similarly implemented based on data derived from the motion detected by the activity band.

At block 820 the process determines whether an activity having ergonomic implications has been identified. We will call it an ergonomic activity for simplicity. For example, typing has a characteristic rhythm and movement of one finger at a time, which can be detected using a wrist-worn motion detector such as the activity band.

At block 830, the process determines whether the ergonomic activity is continuous. In one embodiment, the ergonomic activity is continuous if the breaks between the ergonomic activity and non-ergonomic activity intervals are below a certain threshold. For example, in one embodiment, for typing it is considered continuous if there are continuous stretches of at least five minutes of typing, where discontinuity is set at 30 seconds. That is, if the user is continuously typing and pausing for 30 seconds or less, the system detects that as continuous. Other standards and settings may be made, based on ergonomic principles, user preferences, enterprise preferences, etc.

If the ergonomic activity is not continuous, the process ends, at block 840. In one embodiment, the process ends if the pause in the ergonomic activity is sufficiently long to have terminated the activity, and thus reset the motion identification.

If the ergonomic activity is continuous, the process continues to block 850. At block 850, the process monitors the motion to determine ergonomics. In one embodiment, this may include waking up a higher power processor to monitor motions. In one embodiment, this includes comparing the motions to an ergonomically correct pattern and/or an ergonomically incorrect pattern.

At block 860, the process determines whether the user's motions need adjustment. In general, if the user's motions are ergonomically incorrect, there are certain adjustments to move the motion closer to the proper format. For example, if the user's wrists are not in the proper position during typing, a small adjustment may be enough.

If adjustment is needed, at block 870, the user is alerted. In one embodiment, the alert may be visual, tactile, or auditory. In one embodiment, a message may be sent to the user in another format. In one embodiment, if the activity band can be coupled to a computing device, the activity band may communicate the alert to the computing device. In one embodiment, if a tactile alert may be used to adjust the user's stance to an ergonomically preferred format, it may be the preferred mode of feedback. After alerting the user, the process continues to block 830, to continue monitoring the motions as long as the ergonomic activity remains continuous.

If no adjustment is needed, in one embodiment the process determines whether it is time to stretch or otherwise move from the ergonomic activity. If so, a user alert is given. Otherwise, the process continues to block 830 to continue monitoring.

Figure 9A:
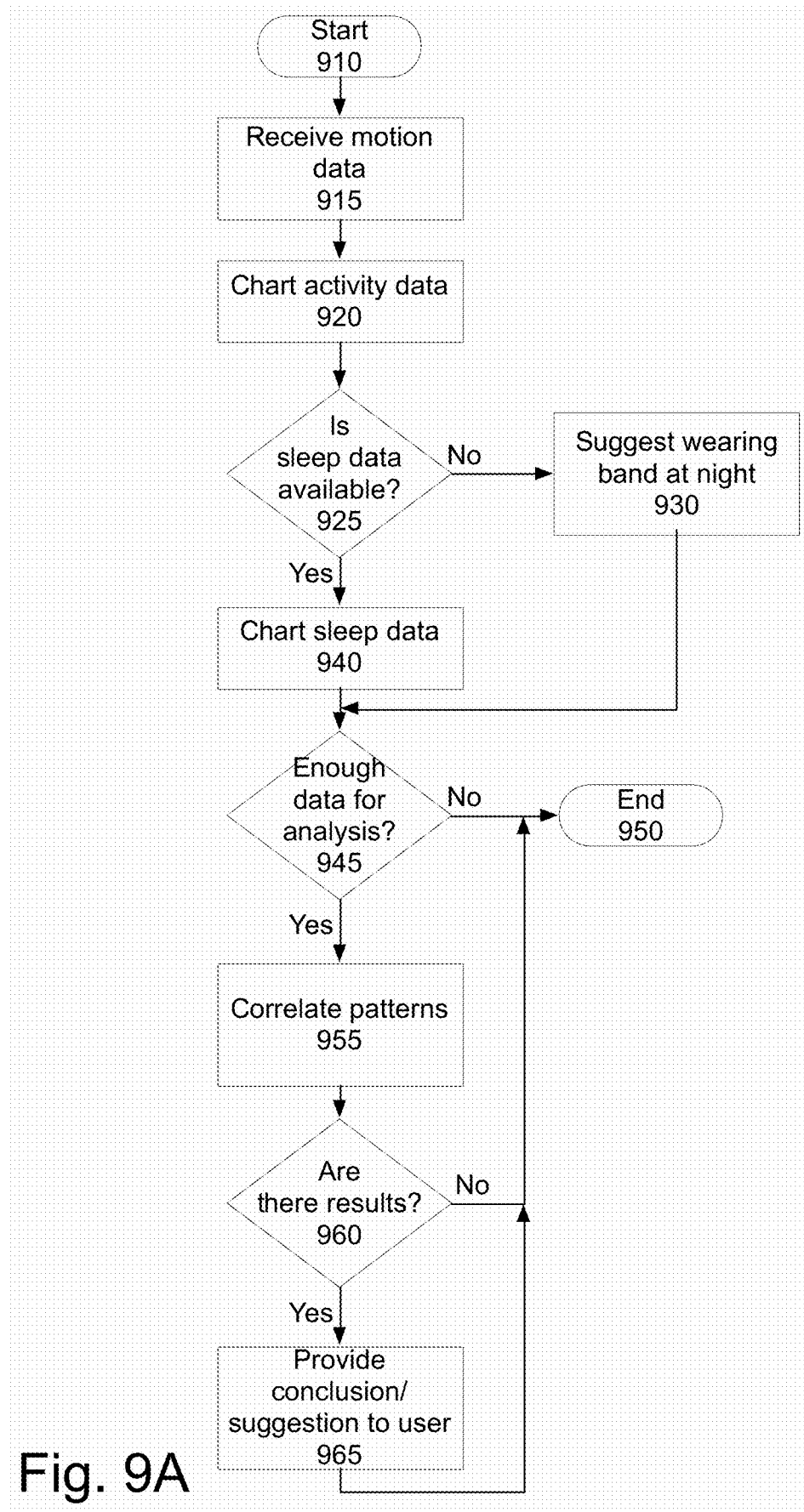
FIG. 9A is a flowchart of one embodiment of correlating based on activity data.

FIG. 9A is a flowchart of one embodiment of correlating based on activity data. The process starts at block 910. In one embodiment, this analysis is done on a computing device to which the data from the activity band is uploaded. In another embodiment, this process may take place on the activity band itself. In one embodiment, the analysis may be split between the activity band, local computing device, and/or server device.

At block 915, motion data is received. In one embodiment, the motion data reflects motion data from at least one day. Alternatively, the motion data reflects at least one week of data. Alternatively, the motion data reflects a block of motion o the same type (e.g. a completed activity, such as a "session of typing," (ergonomic activity) a "sport activity" (vigorous activity) or a "walk" (daily activity), etc. Alternatively, the motion data reflects a smaller time block.

At block 920, the activity data is charted. FIGS. 2A and 2B illustrate two embodiments of such charts of activity data.

At block 925, the process determines whether sleep data is available. If no sleep data is available, the process at block 930 suggests that the user wear the activity band at night. The process then continues to block 945. If the user has provided sleep data, the sleep data is charted at block 940. The process then continues to block 945.

At block 945, the process determines whether there is enough data for analysis. In one embodiment, the "data" which is available for analysis is all previously recorded data, not just the current set of data. In one embodiment, correlation with any level of confidence requires at least a certain level of data. For example, in one embodiment, in order to correlate athletic performance and activity level, at least one week of data is needed. Similarly, in order to correlate sleep quality with activity level, a plurality of observations, at various activity levels (and in one embodiment times and/or intensity associated with the activities) is needed. If there is not enough data, the process ends at block 950. In one embodiment, the user is informed that additional data is needed before correlations can be formed.

If there is sufficient data, at block 955 the patterns are correlated. In one embodiment some or all of the following correlations may be evaluated:

If there is sufficient data, at block 955 the patterns are correlated. In one embodiment some or all of the following correlations may be evaluated:
  sleep quality and activity level
  speed of falling asleep and activity level
  performance sport performance and overall activity level
  performance sport performance and sleep level
  ergonomic patterns and activity level Other correlations based on the motion data, other observed data, and user's characteristics may further be created.

At block 960, the process determines whether there are results. There may not be results if there is no consistent correlation. If there are no results the process ends at block 950. In one embodiment, the user may be informed that no correlation has been found yet, but recommending that the user continue wearing the band during the day and night.

If there are results, at block 965 the conclusions/suggestions are provided to the user. For example, the user may be informed that his or her sport performance is improved when there was a medium level of activity the two days prior to the performance sport activity, and a low level of activity the day before the activity. For another example, the user may be informed that he or she sleeps better when he or she performs at least 30 minutes of vigorous activity more than three hours before going to sleep. Other types of suggestions may be made, based on the correlations calculated. The process the ends at block 950.

This type of correlation can generally not be performed by other types of devices. Most performance sport monitors only monitor while the user is doing the sport. Most sleep monitors only monitor while the user is sleeping. Thus, this correlation is only made possible by having an activity band which is designed to be worn through all types of activities, through the day and night, and which can analyze this data to identify patterns, and calculate correlations. In one embodiment, the above process is performed through a neural-network type system. In one embodiment, another model may be used.

Figure 9B:
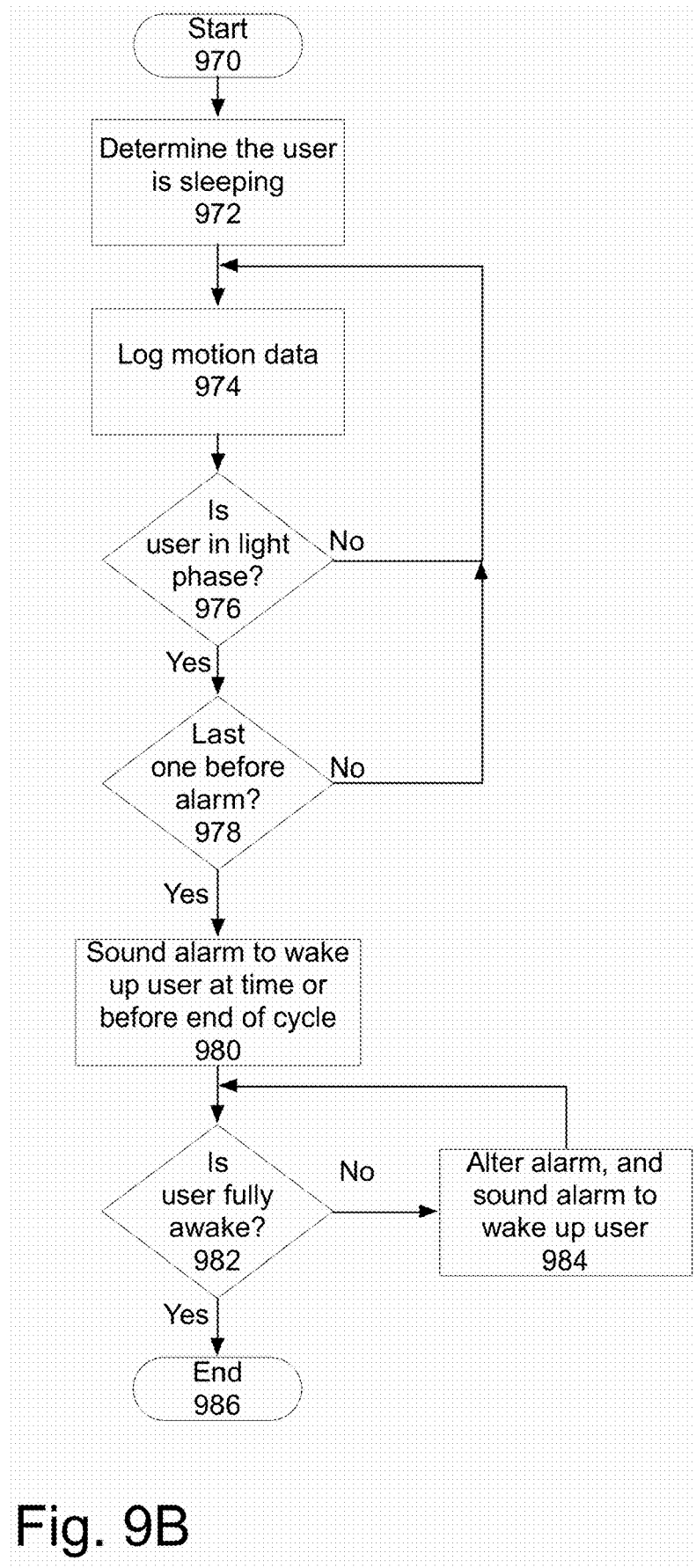
FIG. 9B is a flowchart of one embodiment of using sleep data for waking up the user.

FIG. 9B is a flowchart of one embodiment of using sleep data for waking up the user. The process starts at block 970. At block 972 the process determines that the user is sleeping. At block 974, the motion data is logged. At block 976 the process determines whether the user is in the light phase of sleep. If the user is in deep sleep, the process returns to block 974 to continue logging the motion data.

If the user is in a light sleep phase, the process continues to block 978. At block 978 the process determines whether this light sleep cycle is likely to be the last one before the alarm (e.g. before the user should be getting up). In one embodiment, the alarm is set by the user. In another embodiment, the alarm is calculated based on a known sleep length and usual wake-up time. If this is not the last cycle, the process returns to block 974 to continue logging the motion data.

If this is likely to be the last cycle, the process continues to block 980. At block 980, the alarm is sounded to wake up user at the designated time (e.g. 6:30 am) within the current light sleep cycle, or before the end of the light sleep cycle (e.g. before the user moves into a deeper sleep cycle), for example at 6:25. While this may mean the user is alerted earlier than his or her normal waking time, waking from the light sleep cycle is a better experience than waking from a deeper cycle. Therefore, losing some sleep time is generally worth the overall more restful sleep and peaceful waking provided by this method.

At block 982, the process determines whether the user is fully awake. If so, the process ends at block 986. If the user is not yet fully awake, a different alarm is sounded, at block 984. The process then continues to block 982, to continue monitoring whether the user is fully awake.

One of the advantages of having an activity band to monitor sleep is that the alarm need only be sounded when the user is not yet awake and moving. Furthermore, in one embodiment, the alarm may be tactile or otherwise low impact on other individuals in the room. By using the activity band for the alarm, the other users will not be woken up by the alarm ringing after the person who needs to be woken up has gotten out of bed.

FIG. 10 is a chart of one embodiment of the uses of the activity band. The uses include activity-based uses, e.g. encouraging the user to a level of healthy activity. Such encouragement may include coaching, tracking information, correlating statistics, etc. The social networking aspects of the band may also be part of the encouragement of the users. The social networking aspects may include providing visual feedback of the user's activity status, correlating timing for movement or stretching, automatic uploading of data for competitions or similar activities to a shared social network. The shared social network may be a custom network associated with the activity band, or an existing social site such as FACEBOOK™, TWITTER™, etc.

The activity band may also provide monitoring of various types. The monitoring may further include correlating such things as sleep patterns and exercise levels, ergonomics and sleep patterns, sleep patterns and performance in sports, etc. Generally, people don't realize how much one aspect of their life and behavior affects another. For example, some people may need eight hours of sleep to perform optimally at a performance sport. Some people may sleep better or deeper if they exercise at a certain time of day before sleeping, etc. All these patterns can be unique to the user, and determined by correlating observed data from the activity band.

In addition to activity-based uses for the activity band, the activity band may also be used as an access pass in one embodiment. An access pass, in one embodiment, provides access to buildings, devices, etc. A magnetic, RF (radio frequency), or RFID (radio frequency identifier), or another mechanism may be included within the activity band and used to enable the activity band to be an access device.

Additionally, the activity band may provide identification, replacing a badge in an enterprise setting. This may be done by printing on the activity band itself, in one embodiment.

Additional uses for the band, taking advantage of its always-worn, always monitoring movement data, aspects may be added without departing from the underlying concept of the present invention.

Figure 11:
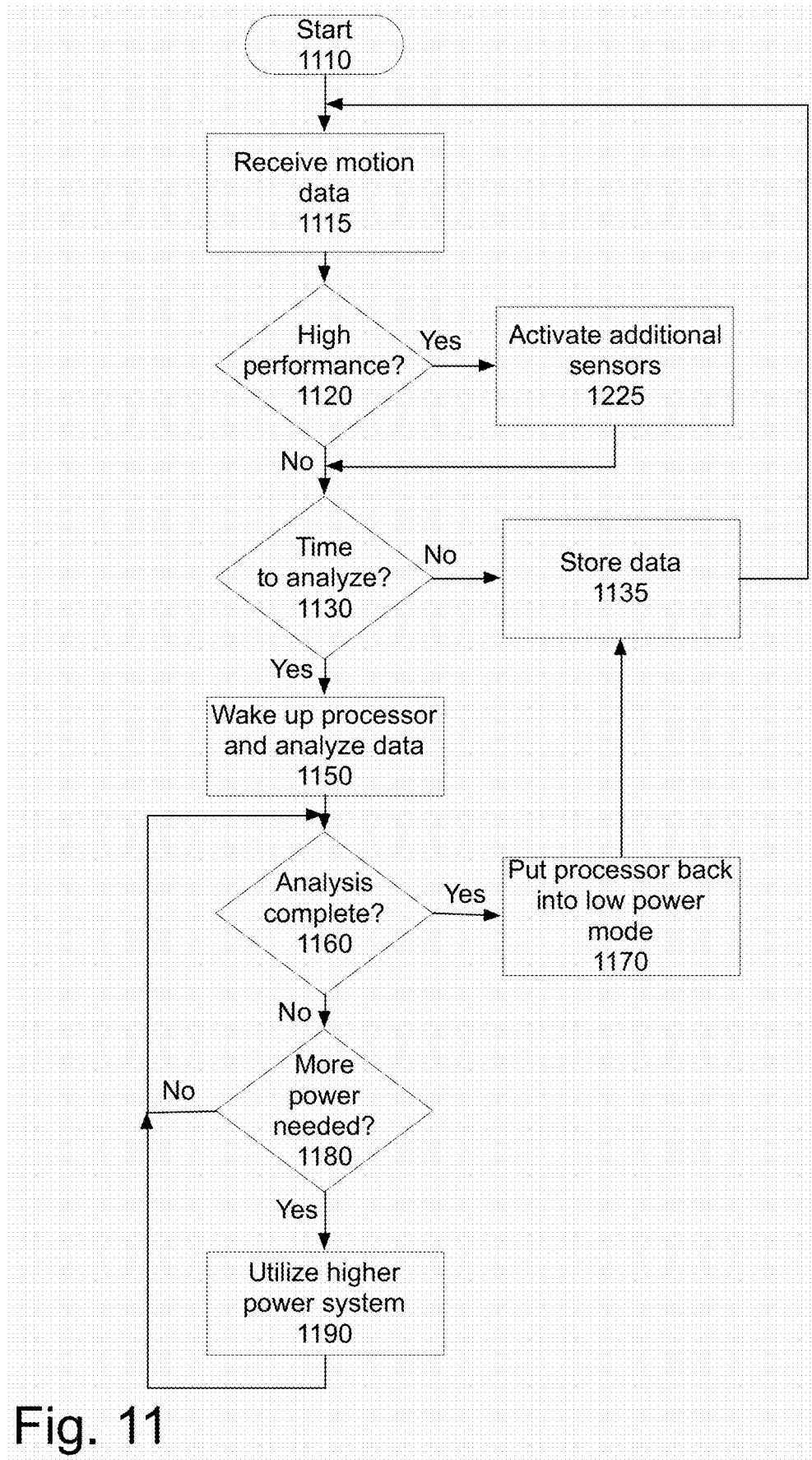
FIG. 11 is a flowchart of one embodiment of power management in the activity band.

FIG. 11 is a flowchart of one embodiment of power management in the activity band. The process starts at block 1110. In one embodiment, power management is an always-on system to maximize battery life within the activity band. While the term "battery" is used, whatever the power supply is, the process may be implemented to minimize power consumption.

At block 1115, motion data is received. Motion data is received continuously by the system, in one embodiment.

At block 1120, the process determines whether the system is in high performance mode. In one embodiment, high performance mode occurs when the activity level of the user indicates particular types of activities, such as bicycling, running, or similar activities for which the use of additional sensors would be helpful. If it is high performance, the process at block 1225 activates the additional sensors. In one embodiment, those sensors may include one or more of: barometric sensors, compass sensor, gyroscopes, additional accelerometers, GPS (global positioning system) sensors, etc. The process then continues to block 1130. If the current activity level is not high performance, the process continues directly to block 1130.

At block 1130, the process determines whether it is time to analyze the data. As noted above, analysis occurs periodically, and that period may be based on various things. At its most power efficient, the period may be based on a timer, which requires no additional analysis and very little power overhead. If it is not yet time to analyze the data, the data is stored at block 1135, and the process returns to block 1115 to continue receiving data. In another power efficient mode, the analysis is done only when the activity band is connected to power, or coupled to a computing device.

If it is time to analyze the data, the process continues to block 1150. At block 1150, the process wakes up the processor, to analyze the data. In one embodiment, there is a low power subsystem which can determine whether it is time to analyze, and can obtain motion and/or other sensor data and store that data in memory. There is a higher power subsystem which can analyze the data, compare it to thresholds, and control output mechanisms, if needed. The higher power processor is only activated when it is needed, to minimize power consumption.

At block 1160, the process determines whether the analysis is complete. If so, the processor is placed back into low power mode at block 1170. In one embodiment, if user feedback is needed, and the user feedback is shown on a power-consuming device (e.g. electronic paper, LCD, LED lights), after the analysis is complete the process may determine whether the user feedback needs to be shown, and activate those aspects. In one embodiment, one of the higher power functions provided is the user interface. Thus, in one embodiment, the user interface is low powered (e.g. electronic paper which is only powered when it is being changed) or only turned on periodically.

Once the user feedback is provided, and the processor is thus no longer needed, the high power processor is placed back into sleep mode, at block 1170. The process then continues to block 1135, to store the data. In one embodiment, the processed data (e.g. the result of the processor's analysis, is stored. The process then returns to block 1115 to continue receiving data. Note that generally, the receiving and storing of data is independent of the analysis, and occurs continuously even while the analysis is happening.

If the analysis is determined not to be complete, at block 1180 the process determines whether more power is needed. In one embodiment, analysis may be complex based on multiple factors, as discussed above. In one embodiment, the complexity of the analysis depends on the user preferences. If more power is not needed, the process returns to block 1160. If more power is needed, the process continues to block 1190.

At block 1190, a higher power system is utilized. IN one embodiment, there is a higher power processor within the activity band which may be woken up to be used for such processes. In another embodiment, the higher power system may be a remote device, e.g. a computing device to which the activity band may be linked. In on one embodiment, the activity band may provide feedback to the user that the activity band should be coupled to the computing system to complete analysis. The process then continues to block 1160 to determine whether the analysis is complete.

FIG. 12 is a diagram showing one embodiment of the user interface features which may be incorporated into the activity band. The user interface methods may include various tactile, audio, visual interfaces. In one embodiment as technology develops additional types of interfaces which can be used (e.g. smell or taste-based interfaces) such interfaces may be added to the system without changing the functionality of the system.

Figure 13:
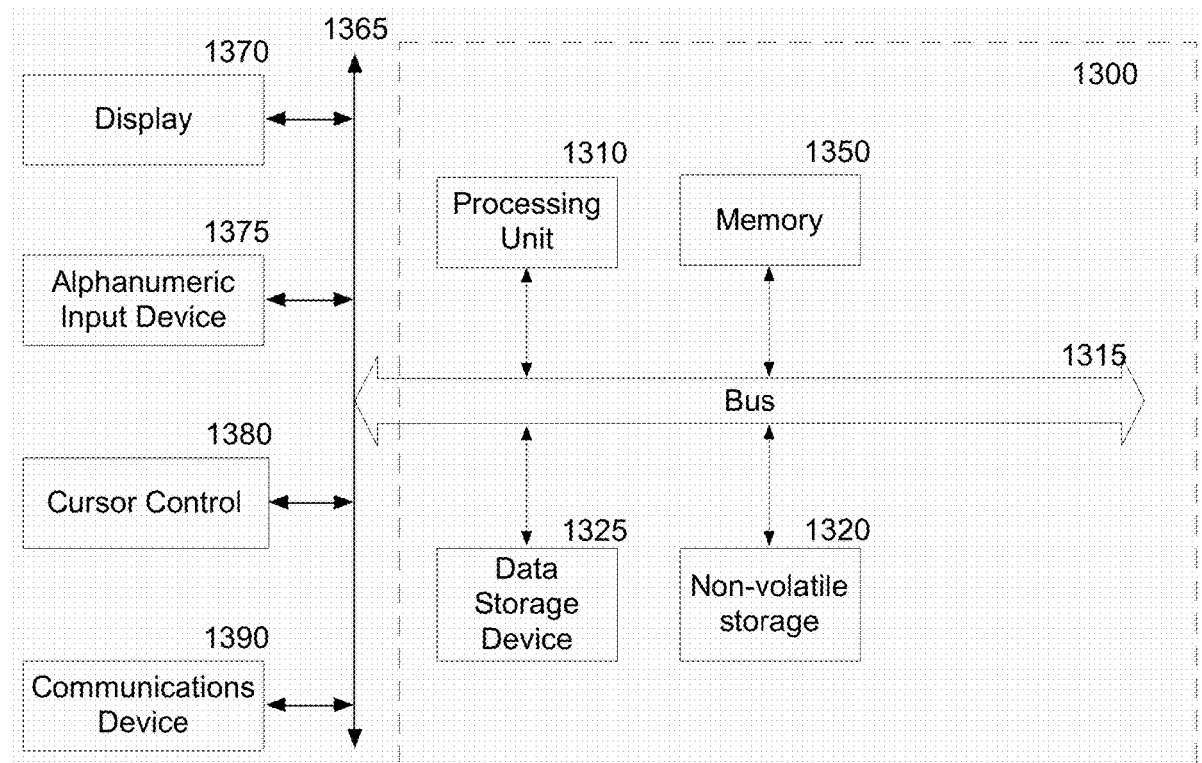
FIG. 13 is a block diagram of one embodiment of a computing system which may be implemented within the activity band.

FIG. 13 is a block diagram of one embodiment of a computing device which may be the activity band, or the computing device with which the activity band interfaces. It will be apparent to those of ordinary skill in the art, however that other alternative systems of various system architectures may also be used.

The data processing system illustrated in FIG. 13 includes a bus or other internal communication means 1315 for communicating information, and a processor 1310 coupled to the bus 1315 for processing information. The system further comprises a random access memory (RAM) or other volatile storage device 1350 (referred to as memory), coupled to bus 1315 for storing information and instructions to be executed by processor 1310. Main memory 1350 also may be used for storing temporary variables or other intermediate information during execution of instructions by processor 1310. The system also comprises in one embodiment a read only memory (ROM) and/or static storage device 1320 coupled to bus 1315 for storing static information and instructions for processor 1310, and a data storage device 1325 such as a magnetic disk or optical disk and its corresponding disk drive, or Flash memory or other storage which is capable of storing data when no power is supplied to the system. Data storage device 1325 in one embodiment is coupled to bus 1315 for storing information and instructions.

The system may further be coupled to a display device 1370, such as a cathode ray tube (CRT) or a liquid crystal display (LCD) coupled to bus 1315 through bus 1365 for displaying information to a computer user. An alphanumeric input device 1375, such as a keyboard including alphanumeric and other keys, may also be coupled to bus 1315 through bus 1365 for enabling a user to communicate information and command selections to processor 1310. An additional user input device may further be included. One such user input device is cursor control device 1380, such as a mouse, a trackball, stylus, or cursor direction keys may be coupled to bus 1315 through bus 1365 for communicating direction information and command selections to processor 1310, and for controlling cursor movement on display device 1370.

Another device, which may optionally be coupled to computer system 1300, is a communication device 1390 for accessing other nodes of a distributed system via a network. The communication device 1390 may include any of a number of commercially available networking peripheral devices such as those used for coupling to an Ethernet, token ring, Internet, or wide area network, personal area network, wireless network or other method of accessing other devices. The communication device 1390 may further be a null-modem connection, or any other mechanism that provides connectivity between the computer system 1300 and the outside world. Note that any or all of the components of this system illustrated in FIG. 13 and associated hardware may be used in various embodiments of the present invention.

It will be appreciated by those of ordinary skill in the art that the particular machine which embodies the present invention may be configured in various ways according to the particular implementation. The control logic or software implementing the present invention can be stored in main memory 1350, mass storage device 1325, or other storage medium locally or remotely accessible to processor 1310.

It will be apparent to those of ordinary skill in the art that the system, method, and process described herein can be implemented as software stored in main memory 1350 or read only memory 1320 and executed by processor 1310. This control logic or software may also be resident on an article of manufacture comprising a computer readable medium having computer readable program code embodied therein and being readable by the mass storage device 1325 and for causing the processor 1310 to operate in accordance with the methods and teachings herein.

The present invention may also be embodied in a handheld or portable device containing a subset of the computer hardware components described above. For example, the handheld device may be configured to contain only the bus 1315, the processor 1310, and memory 1350 and/or 1325. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 1310, a data storage device 1325, a bus 1315, and memory 1350, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1310. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

Figure 14:
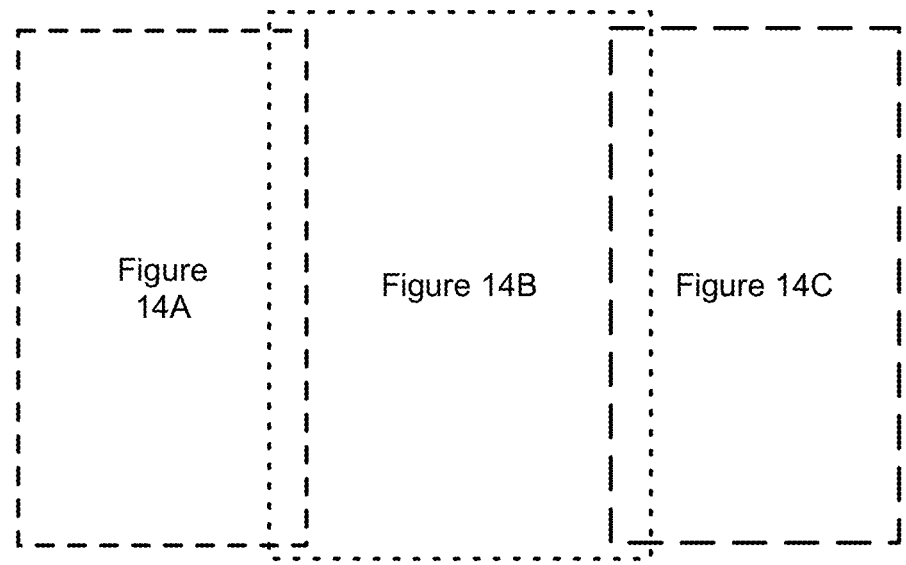
FIG. 14 is diagram showing how the elements of the circuit diagram shown in FIGS. 14A-14C fit together.
Figure 14A:
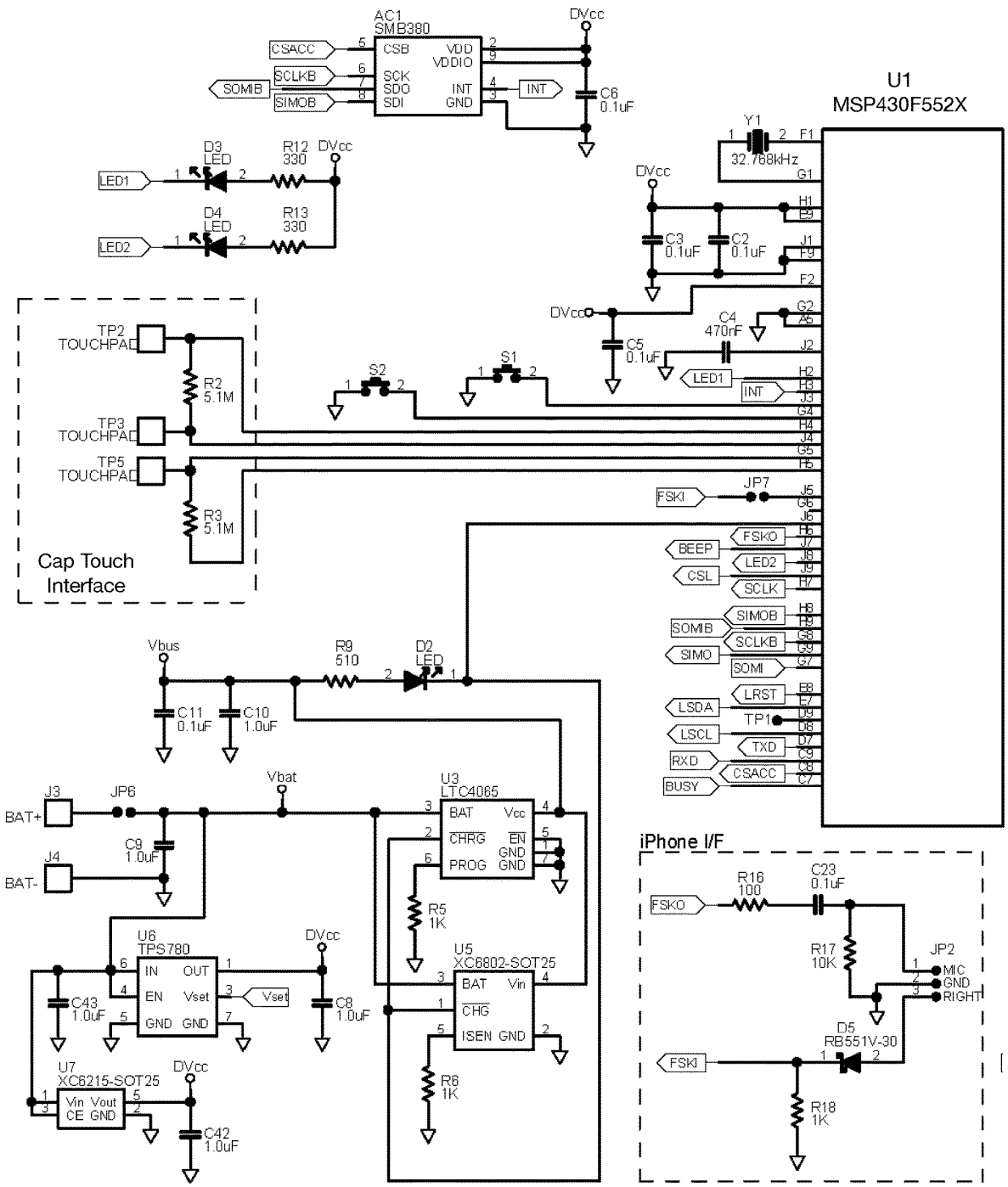
FIGS. 14A-14C together show one embodiment the circuit diagram for the activity band.
Figure 14B:
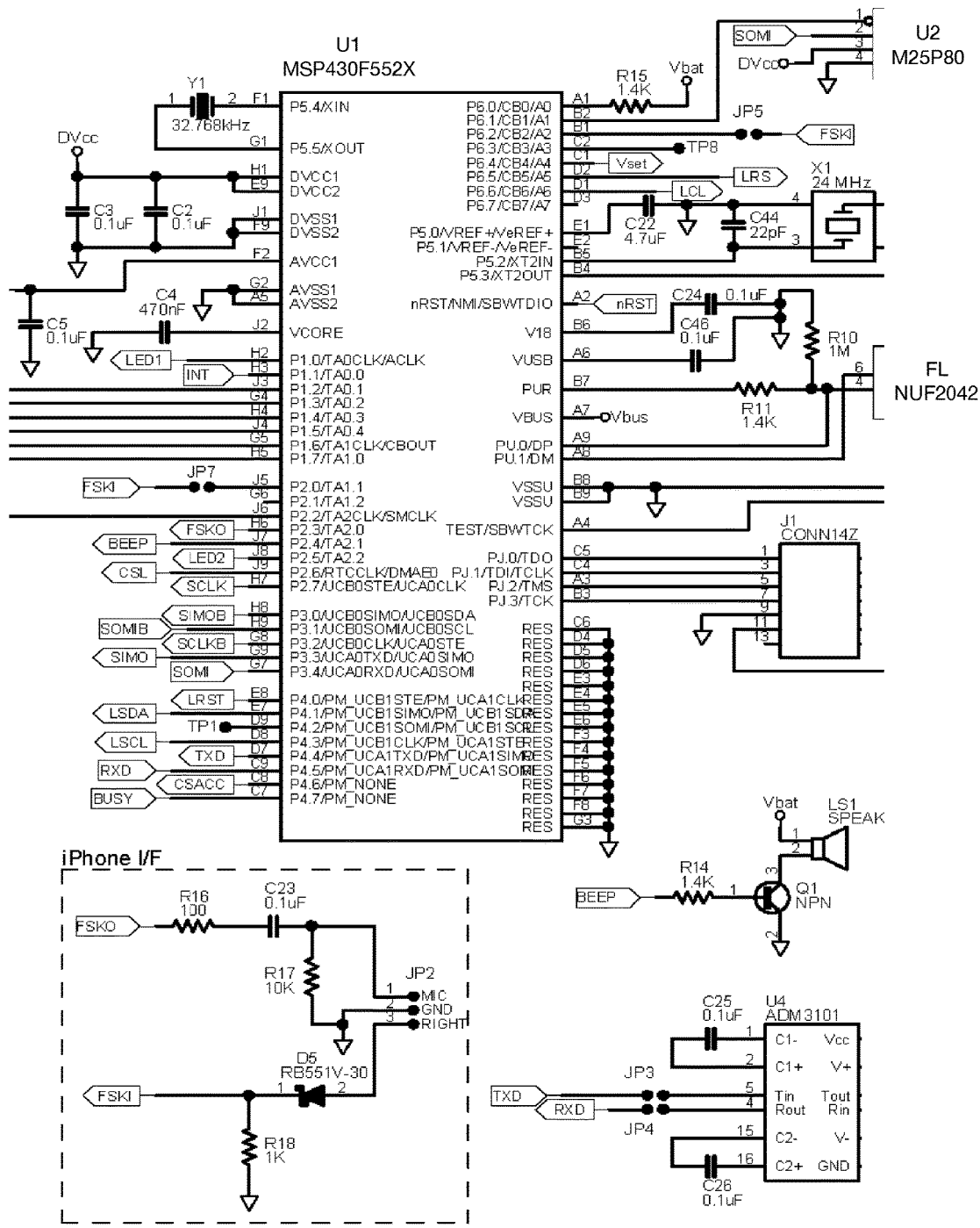
Figure 14C:
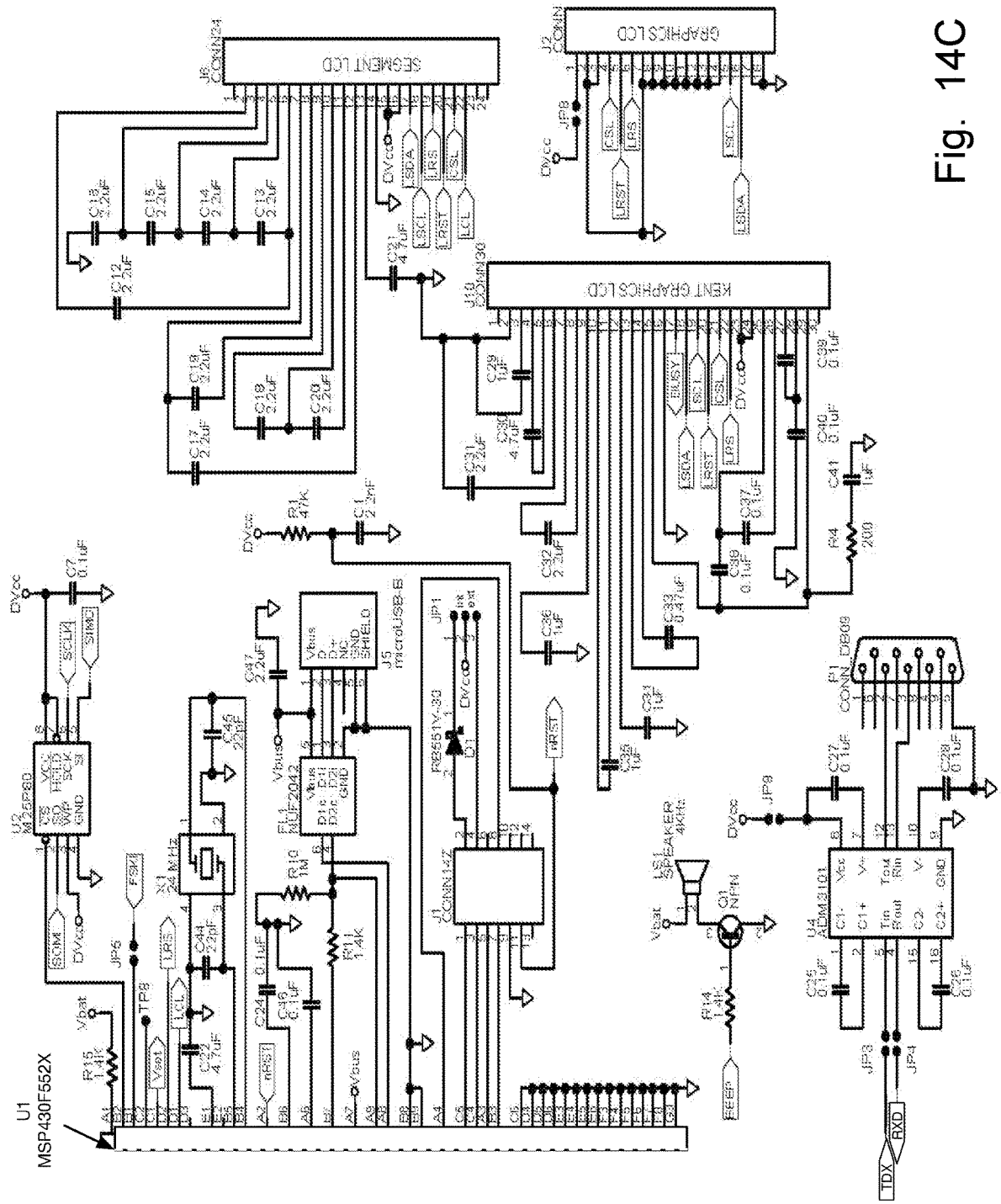

FIGS. 14A-14C together form a single circuit diagram of one embodiment of the activity band. The circuit diagram is split in a way to enable one to put it together by aligning the sides of the pages, to form a single continuous image, showing the circuit diagram of one embodiment of the activity band. The relationship of the elements shown in FIGS. 14A-14C is shown in FIG. 14.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method of monitoring a user's activity level and improving the user's health with a wearable device, the method comprising:
   determining, by the wearable device, that the user is wearing the wearable device, and monitoring movements of the user using a motion sensing system in the wearable device;
   identifying, by the wearable device, a user activity based on the movements of the user, the wearable device capable of identifying all of: a daily activity involving steps taken by the user, an aerobic exercise activity by the user, a repetitive ergonomic activity by the user, and non-movement of the user, wherein the identifying the user activity determines both that the activity is repetitive and that it is ergonomic;
determining non-movement of the user for a first preset period of time, by the wearable device, and alerting the user to move;
determining, by the wearable device, when the user has been performing the repetitive ergonomic activity for a second preset period of time in a non-ergonomic manner by comparing the monitored movements to an ergonomically correct pattern, and alerting the user to adjust his movements,
both determining that the user is wearing the wearable device and determining non-movement of the user being performed in an always-on manner throughout the user's day;
determining, by the wearable device, whether the user is taking steps, and counting the steps;
identifying, by the wearable device, the aerobic exercise activity, and tracking the aerobic exercise activity; and
comparing the daily activity, the aerobic exercise activity, the repetitive ergonomic activity, and periods of non-movement to user goals, and informing the user via the wearable device whether the user goals have been met, the user goals including a plurality of: activity levels, ergonomic levels, and sleep levels.

2. The method of claim 1, wherein the identified repetitive ergonomic activity is typing.

3. The method of claim 2, further comprising:
enabling the user to activate ergonomic activity alerts for a plurality of potential ergonomic activities.

4. The method of claim 1, wherein the non-movement alerting comprises an indication that the user should move, stretch, focus away, or otherwise alter the ergonomic activity for improved health.

5. The method of claim 1, further comprising:
receiving data from another device associated with the user, the other device located on another body location of the user; and
determining the ergonomic activity based on data from the wearable device and the another device.

6. The method of claim 1, further comprising:
informing the user that the user is not on track to meet the user goals, and suggesting changes in behavior.

7. The method of claim 1, further comprising:
tracking the user's sleep patterns; and
correlating the sleep patterns, counted steps, the aerobic exercise activity, and periods of non-movement to make recommendations to the user.

8. The method of claim 1, wherein the determining of repetitive ergonomic activity is further performed throughout the night.

9. The method of claim 1, wherein the user may activate or deactivate the wearable device and wherein the monitoring only occurs when the device is activated.

10. A wearable device to monitor a user's activity level, and improve the user's health comprising:
a motion sensor to receive motion data;
a motion data processor to determine whether the user is wearing the wearable device, and monitoring movements of the user using a motion sensing system in the wearable device;
the motion data processor to identify a user activity based on the movements of the user, wherein the identifying the user activity determines both that the activity is repetitive and that it is ergonomic;
an ergonomic analysis logic to determine, based on the data from the motion sensor, when the user has not moved from a repetitive ergonomic activity in a period of time and is moving in a non-ergonomic manner by comparing the monitored movements to an ergonomically correct pattern, and a first user interface to alert the user to adjust his movements, wherein the analysis logic determines both that the activity is repetitive and that it is ergonomic, the determining whether the user is wearing the wearable device being performed in an always-on manner throughout the user's day;
an activity analysis logic to track user steps associated with daily activities and predefined movements associated with exercise activities, based on the data from the motion sensor;
a correlation logic to compare the steps of the daily activities, the predefined movements of the exercise activity, and periods of non-movement to user goals, the user goals including a plurality of: activity levels, ergonomic levels, and sleep levels; and
a second user interface to provide data on whether the user goals were met to the user.

11. The wearable device of claim 10, wherein the identified repetitive ergonomic activity is typing.

12. The wearable device of claim 10, further comprising:
a user interface to enable the user to activate alerts for a plurality of potential ergonomic activities.

13. The wearable device of claim 10, wherein the alerting comprises an indication that the user should move, stretch, focus away, or otherwise alter the ergonomic activity for improved health.

14. The wearable device of claim 10, further comprising:
a device connection logic to receive data from another device associated with the user, the other device located on another body location of the user; and
the ergonomic analysis logic to use the data from the other device and the motion sensor to determine the ergonomic activity.

15. The wearable device of claim 10, further comprising:
the user interface to inform the user that the user is not on track to meet the user goals, and suggesting changes in behavior.

16. The wearable device of claim 10, further comprising:
a sleep analysis logic to track the user's sleep patterns; and
the correlation logic to correlate the sleep patterns, counted steps, the aerobic exercise activity, and periods of non-movement to make recommendations to the user.

17. A system to monitor a user's activity level and improve the user's health comprising:
a wearable device comprising:
a motion sensor to receive motion data;
a motion data processor to determine whether the user is wearing the wearable device, and monitoring movements of the user using a motion sensing system in the wearable device the motion data processor to identify a user activity based on the movements of the user, wherein the identifying the user activity determines both that the activity is repetitive and that it is ergonomic;
an ergonomic analysis logic to determine, based on the data from the motion sensor, when the user has been performing a repetitive ergonomic activity for a period of time in a non-ergonomic manner by comparing the monitored movements to an ergonomically correct pattern, and a user interface to alert the user to adjust his movements, the determining whether the user is wearing the wearable device being performed in an always-on manner throughout the user's day;
an activity analysis logic to track a daily activity and an exercise activity of the user; and a user interface to provide information to the user based on data from the ergonomic analysis logic and the activity analysis logic, informing the user whether user goals have been met, the user goals including a plurality of: activity levels, ergonomic levels, and sleep levels.

18. The system of claim 17, wherein the ergonomic activity comprises being inactive, and the ergonomic analysis logic prompts an alert to the user after a period of inactivity.

19. The system of claim 17, further comprising:
a correlation logic to determine whether the user is meeting the user goals, based on data from the activity analysis logic and the ergonomic analysis logic, and to generate an alert to the user that the user is not on track, suggesting changes in behavior.

20. The system of claim 17, further comprising:
a sleep analysis logic to track a user's sleep patterns; and
the correlation logic to correlate the sleep patterns, counted steps, the aerobic exercise activity, and periods of non-movement to make recommendations to the user.

21. The system of claim 17, further comprising:
a server to store data from the wearable device, and to provide access to detailed views of the data.

22. The system of claim 17, wherein the repetitive ergonomic activity comprises typing.

* * * * *